(12) United States Patent
Hilliard

(10) Patent No.: US 7,950,131 B2
(45) Date of Patent: May 31, 2011

(54) ROBOTIC SYSTEM FOR FORMING FEATURES IN ORTHODONTIC ALIGNERS

(76) Inventor: Jack Keith Hilliard, Lakeland, FL (US)

( * ) Notice: Subject to any disclaimer, the term of this patent is extended or adjusted under 35 U.S.C. 154(b) by 874 days.

(21) Appl. No.: 11/936,215

(22) Filed: Nov. 7, 2007

(65) Prior Publication Data

US 2008/0141534 A1    Jun. 19, 2008

Related U.S. Application Data

(60) Provisional application No. 60/870,696, filed on Dec. 19, 2006.

(51) Int. Cl.
*B23P 23/00* (2006.01)
*A61C 7/02* (2006.01)
*B29C 51/42* (2006.01)
*B29C 53/00* (2006.01)
*B29C 37/02* (2006.01)
*B29C 35/00* (2006.01)

(52) U.S. Cl. ..... 29/564; 29/33 A; 29/896.11; 425/174.4; 425/193; 425/375; 425/384; 433/6

(58) Field of Classification Search .................. 29/564, 29/38 A, 38 C, 33 A, 896.11; 425/174.4, 425/806, 193, 384, 385, 375; 264/16; 433/6; 72/342.1, 342.94
See application file for complete search history.

(56) References Cited

U.S. PATENT DOCUMENTS

| | | | |
|---|---|---|---|
| 2,531,222 A | 11/1950 | Kesling | |
| 4,894,012 A | 1/1990 | Goldberg et al. | |
| 5,139,419 A | 8/1992 | Andreiko et al. | |
| 5,447,432 A | 9/1995 | Andreiko et al. | |
| 5,683,243 A | 11/1997 | Andreiko et al. | |
| 5,692,894 A | 12/1997 | Schwartz et al. | |
| 5,975,893 A | 11/1999 | Chishti et al. | |
| 6,103,173 A | 8/2000 | Kastl et al. | |
| 6,247,631 B1 | 6/2001 | Kawakatsu et al. | |
| 6,293,790 B1 | 9/2001 | Hilliard | |
| 6,398,548 B1 | 6/2002 | Muhammad et al. | |
| 6,616,444 B2 | 9/2003 | Andreiko et al. | |
| 6,702,575 B2 | 3/2004 | Hilliard | |
| 6,732,558 B2 | 5/2004 | Butscher et al. | |
| 6,776,614 B2 | 8/2004 | Wiechmann et al. | |
| 6,814,574 B2 | 11/2004 | Abolfathi et al. | |
| 6,846,179 B2 | 1/2005 | Chapouland et al. | |
| 6,928,733 B2 | 8/2005 | Rubbert et al. | |
| 7,077,646 B2 | 7/2006 | Hilliard | |
| 7,092,784 B1 * | 8/2006 | Simkins | 700/163 |
| 7,283,891 B2 | 10/2007 | Butscher et al. | |

(Continued)

OTHER PUBLICATIONS

ThermoAire™ Instruction Manual from Raintree Essix, copyright 2005 with an indicated revision date of Apr. 2005, 16 pages.*

(Continued)

*Primary Examiner* — Erica E Cadugan
(74) *Attorney, Agent, or Firm* — Dorr, Carson & Birney, P.C.

(57) ABSTRACT

A robotic system for forming features in orthodontic aligners includes a control system, a platen for three-dimensional positioning of the aligner, a heating station for selectively heating a small region of the aligner, and a thermoforming station for manipulating the heated region to form a desired feature in the aligner. Optionally, a laser cutting and trimming station can also be included to trim excess material from the aligner or to cut features into the aligner. The control system can include a processor with CAD software to enable a user to design features for aligners.

14 Claims, 14 Drawing Sheets

U.S. PATENT DOCUMENTS

| | | | |
|---|---|---|---|
| 2001/0009753 A1 | 7/2001 | Chishti et al. | |
| 2002/0192617 A1 | 12/2002 | Phan et al. | |
| 2003/0070468 A1* | 4/2003 | Butscher et al. | 72/295 |
| 2003/0190575 A1 | 10/2003 | Hilliard | |
| 2003/0190585 A1 | 10/2003 | Sun et al. | |
| 2004/0115586 A1 | 6/2004 | Andreiko et al. | |
| 2005/0082703 A1* | 4/2005 | Wrosz | 264/16 |
| 2006/0093982 A1 | 5/2006 | Wen | |
| 2006/0188834 A1 | 8/2006 | Hilliard | |
| 2006/0275731 A1 | 12/2006 | Wen et al. | |
| 2007/0178423 A1 | 8/2007 | Rubbert et al. | |

OTHER PUBLICATIONS

Hakko, Hakko 851 [online] [retrieved on Sep. 3, 2004] <URL: http://www.hakko.com/itnl/product.html? catID=8&prodID=35>.

* cited by examiner

ROBOTIC SYSTEM FOR FORMING FEATURES IN ORTHODONTIC ALIGNERS

RELATED APPLICATION

The present application is based on and claims priority to the Applicant's U.S. Provisional Patent Application 60/870,696, entitled "Robotic System For Forming Features in Orthodontic Aligners," filed on Dec. 19, 2006.

BACKGROUND OF THE INVENTION

1. Field of the Invention

The present invention relates generally to the field of orthodontics. More specifically, the present invention discloses a robotic system for forming features in orthodontic aligners.

2. Prior Art

The present invention involves the convergence of multiple technologies that in combination present a novel mechanical system for robotically fabricating a type of orthodontic appliance known as a polymeric shell aligner. The present invention represents integration of certain 3D imaging and digital processes into a popular method of orthodontic treatment based on such aligners. The multiple technologies involved in the present invention include digital technologies that have been commercially introduced to the orthodontic field in recent years as well as other known, non-dental industrial technologies developed for the machine tool world and generally for industrial automation and robotic applications. As a new combination of multiple technologies, the present invention enables an automated process for installing activation features and other types of features needed for polymeric shell orthodontic aligners to receive auxiliary devices that serve to expand their usefulness, range and duration of application.

The following is a detailed description of the array of current technologies that are incorporated into the present invention beginning with descriptions of digital technologies currently known and currently in use in orthodontic-related applications. Lastly, a detailed description of how the various technologies are integrated and how the present invention is operated and its functions will be covered.

3D Scanning. Beginning in the early 1990's, various inventors introduced a variety of means for obtaining virtual models of an orthodontic patient's upper and lower dentition and the soft oral tissues. The impetus for obtaining such virtual models is that once available as a digital model, a case becomes available for virtual manipulation through the use of advanced 3D computer-aided design (CAD) software. A patient's occlusion may be corrected to an ideal finished result, and such an ideal computer-based result can then serve as a template for treating the actual case over time. Today, many useful adjuncts to standard orthodontic treatment begin with the step of scanning a patient's teeth to obtain such a virtual model. A high-resolution digital model begins with the scanning process, which can be accomplished in a matter of minutes. Current dental scanning methods include computed axial tomography (CAT) as applied directly to a negative impression of the patient's teeth as well as direct scanning of the dentition using an intra-oral handheld wand-type probe for converting oral realities directly into digital code, and other methods involving laser, optical and CMM-type scanning of a conventional plaster model of a patent's teeth.

Virtual Treatment As referenced earlier, once a virtual model of a patient's pre-treatment malocclusion resides in the virtual CAD environment, the occlusion can be corrected virtually. Virtual correction of the teeth is literally that—a virtual ideal occlusion can be created emulating the condition of the actual teeth and facial structure that would hypothetically result at the end of successful orthodontic treatment. A series of patents issued to Andreiko teach algorithms and a flowchart-type outline of steps for accomplishing virtual correction. Virtual treatment essentially involves the virtual detachment of a tooth (or a group of teeth) from its adjacent teeth and supporting soft tissue and jaw. That tooth or that group of teeth are then virtually tipped, rotated, extruded, intruded or bodily repositioned to an ideal position and orientation. Once all of the teeth are generally repositioned, fine positional adjustments are normally required so that the gnathologic interdigitation of the opposing teeth results in a balanced and stable occlusion. All of the teeth, either individually or in groups, are manipulated in this manner during the virtual treatment process. Aids used in the process can include statistical norms for tooth position and size, standardized prescription values for positional references known as torque, angulation, prominence, rotation and so on as well as arch form templates useful for establishing a natural overall arch shape.

These computer-based methods for creating fully-treated virtual models of an orthodontic patient's teeth have served as the core for new and powerful diagnostic and analytical tools. Commercial services based on such tools have become commercially available to orthodontists. New methods for direct and indirect bracket placement as taught by Doyle et. al. and methods for the machining of custom orthodontic brackets by Andreiko, as well as the creation of a series of progressive polymeric shell appliances and other advances are all based on first taking the step of creating an ideal virtually-corrected occlusion within a 3D CAD virtual environment.

Rapid prototyping. In recent years, processes capable of quickly producing accurate physical models from digital virtual models of a patient's dentition have been integrated into various orthodontics systems. For example, virtually-treated dental models as described above can be grown by sending the digital code representing the model to a rapid prototyping machine. Rapid-prototyping machines can produce precise physical replicas of a patient's dental arches and supportive soft tissue. Just as a model of a patient's pre-existing/pre-treatment condition can be grown, so can models of the virtually-treated finished occlusion as described above. So, through a combination of scanning, virtual treatment and rapid prototyping technologies, it is possible for an orthodontist to obtain models of a patient's dental realities that will exist at the time of completion of the patient's treatment, three years into the future for example.

Aligner-Based Orthodontic Therapy. An important orthodontic technique introduced in the late 1940's by Kesling involved the introduction of the tooth positioner as an orthodontic appliance and an orthodontic treatment method. Based primarily on U.S. Pat. No. 2,531,222, Kesling's tooth positioner was a bulky solid mass of vulcanized rubber that earned a reputation as being bad tasting and uncomfortable. Kesling's applinace was characterized by the presence of precisely-formed negative compartments, shaped and positioned to accept and individually ensconce a patient's teeth. Compartments for both the upper and lower arches were cast into the one-piece appliance. Positioning such an appliance in a patient's mouth involved the patient biting into it thereby pushing the upper and lower teeth fully into their respective compartments.

The principle for achieving desirable tooth movement using Kesling's positioners involved slight positional-biasing of the appliance's tooth receiving compartments. Each of the teeth, once positioned in its corresponding cavity would be urged to move according to the slight out-of-position difference between the actual tooth and its receiving compartment. To gain a clearer picture of how the out-of-position fabrication of Kesling's tooth positioner compartments was achieved, a process known as "resetting the model" was used. A standard plaster model of the teeth would first see the skillful sawing-free of the individual plaster teeth. Once free, they would be bonded back into position with a sticky wax material. The wax material permitted the slight repositioning of the teeth using finger pressure. In this manner the plaster teeth of the model would be positioned in slightly more desirable positions. As a laboratory process, the positioner would be cast over that altered model. At later points in treatment, second and third positioners could be cast after the teeth were further repositioned as allowed by mobility afforded by the sticky wax.

Today's popular aligner-based therapy functions similarly in that the same fundamental tooth-moving mechanism is employed. Individual tooth movement is achieved by capturing each tooth in a positionally-biased compartment. Rather than being formed as a bulky solid block of rubber like Kesling, current aligners are thermo-formed by heating thin, clear, hard, but still resilient plastic sheets. They are created by forming the polymeric sheet tightly down over models of the teeth using heat and pressure (very similar to thermo-forming). After the aligner cools from thermo-forming, it is removed from the model and the excess material is trimmed. FIG. 1 shows an example of a conventional orthodontic aligner 18. U.S. Pat. No. 5,975,893 to Chishti et. al. and its many related patents teach the art of fabricating aligners and many aspects of aligner-based orthodontic therapy.

Aligner-Based Commercial Services. A proliferation of commercial support services has occurred in recent years providing orthodontists with sophisticated, digitally-produced aligners that are custom-produced for their individual patients. These services are based on the scanning, digital imaging and rapid prototyping and thermo-forming technologies described above.

One example of such a service follows. A problem faced by U.S. orthodontists in many states involves the requirement that stone models of a patient's teeth be physically stored for a period of years after the active phase of treatment ends. Doctors usually view storing many hundreds of their patient's models as a challenge, requiring storage space and record keeping. Those doctors may now opt to have their cases digitally archived off-site by an archiving service bureau. To utilize such a service, a doctor will send dental models to an archiving service bureau where they are scanned to produce digital code and then discarded. In the event that a need arises for a physical set of archived models, a rapid prototyping process as described above will be employed to grow the needed models from the stored digital code. The resulting physical models are then shipped back to the doctor as ordered.

Another important service closely related to the current invention has also become available to orthodontists in recent years. Provision of that service begins similarly. First, a set of stone models will sent by the attending orthodontist to a commercial service bureau. There the models are scanned to produce an original (beginning) virtual model of a patient's malocclusion. Once the virtual model is available, it is processed into an ideal finished occlusion as described earlier. Once both the beginning and finished occlusions are established, typically 15 to 20 intermediate virtual occlusions will be created all within a virtual CAD environment. Each of the set of intermediate virtual models will exhibit the teeth being moved sequentially in small, but progressive steps toward the desired finished positions and orientations.

The next step in this process sees the digital code for the beginning, the finished and each of the many intermediate virtual models being sent to a rapid prototyping machine. Physical models (or patterns) for the entire progression will be grown. From those patterns, a sequential series of clear polymeric shell-type aligners will be thermo-formed. The resulting set of aligners is trimmed and sequentially numbered and then shipped as one set to the attending orthodontist. The orthodontist then provides the progressive set of aligners to the patient. The patient is instructed to wear each set of upper and lower aligners for two weeks. After two weeks, the first pair of aligners is discarded and the next set in turn is worn for two weeks and so on throughout the course of treatment. The orthodontist's role in such a treatment regime is limited to monitoring the progress of the aligner-based treatment and to take steps if required to insure that treatment progresses steadily toward the finished result according to the treatment plan.

In terms of the present invention in particular, it is important to note that the digital code representing the virtual models described above can be stored indefinitely as data files in any conventional form which includes magnetic tape, CD, hard drive or flash memory. In principal, any of the rapid prototype-produced patterns can be grown any time it may be needed in the future. Further, the digital code representing the virtual model of the dentition can be stored and subsequently used for other objectives such as for processing according to the present invention.

Aligner Auxiliary Devices. In recent years, aligner-based treatment has become quite popular with doctors and orthodontic patients alike. Aligners are appreciated by patients because they are clear, unobtrusive and they do not interfere with eating or speech and because aligners are removable. Being removable, patients can remove them for important social functions for example if desired. Standard steel braces are of course fixed and are worn throughout treatment. Some school-age patients wear their aligner-type appliances only after school and during sleep. Aligners are popular with doctors because the problems of breakage and patient complaints are reduced and patient cooperation is increased Aligners are thoroughly effective in moving teeth at predictable rates, which enables tighter overall scheduling and practice management.

To appreciate the purpose and benefits of the present invention, the reader should understand that only a portion of aligner-type appliances currently used in orthodontics are produced using the digital scanning, imaging, rapid prototyping and thermo-forming methods described above. As an alternative to those digital processes, aligners can be manually fabricated within an orthodontic practice thereby bypassing any need for outside service bureaus and laboratory services altogether. Doctors who opt to form their own aligners in this manner traditionally begin with standard plaster models of their patient's teeth. Those plaster models serve as patterns for thermo-forming aligners in lieu of the rapid prototyping-produced patterns produced according to the digital methods. In-office thermo-forming is usually accomplished using a certain well-known dental laboratory machine called a BIO STAR machine or similar forming machines. The thin sheets of clear plastic from which aligners are formed are available commercially from numerous commercial sources for those doctors who choose to form their own aligners.

During the intervening decades since Kesling introduced tooth positioners, orthodontists have acquired considerable experience and skill in the use of positioner/aligner-type appliances. In physiological terms, aligners and the tooth positioners that preceded them achieve orthodontic correction through the same mechanisms, so experience with positioners has carried over to the current aligner era to a degree. Given the popularity, acceptance and proliferation of this type of treatment, new ways for directing, amplifying and prolonging the treatment forces that polymeric shell-type aligners generate have been sought. For example, U.S. Pat. No. 6,293, 790, "Heated Orthodontic Pliers," to the present inventor discloses a series of steel dental pliers useful for modifying polymeric shell aligners. They are commercially known and available as Thermoplier® instruments Thermoplier® instruments are a family of handheld instruments that are rapidly heated to a pre-determined temperature. Once heated, they are directed to an aligner to effect local heat softening and thermal flowing (or thermo-forming) of the aligner structure thereby forming various types of alterations and features.

An example of the use of Thermoplier® instruments to augment aligner-based therapy follows. Thermoplier® instruments address a common problem faced by orthodontists. The problem is the difficulty typically encountered in correcting an undesirably rotated tooth. Normally, the positional bias or slight out-of-register relationship between an aligner's tooth-receiving compartment and the living tooth will produce force vectors that are capable of achieving certain types of correction, but correcting undesirable rotations is more difficult. To augment an aligner's capability to fully correct a rotation, a doctor may use one of the set of Thermoplier® instruments to thermo-form a small, sharp, inward facing bump in the structure of the aligner. Such a thermo-formed bump requires skillful positioning in the wall of an aligner. When such a modified aligner is seated in position in the mouth, the presence of the bump will produce a force vector of maximum mechanical advantage to rotate the tooth.

To illustrate the use of such bumps in treatment, consider a disto-lingually rotated maxillary lateral tooth for example. A first bump may be placed at the distal incisal position to contact the tooth on its lingual surface, and a second bump may be formed at the mesial, labial, incisal location of the same compartment. Such a pair of co-working bumps then cooperate to create a coupled rotational force in a mesial-lingual direction according to this example. Such balanced, coupled forces have proven to be very effective in accomplishing rotational correction using aligners. Continuing with this example, a practitioner may first achieve partial rotational correction through the use of a plain, as-formed aligner to allow the positional biases of the aligner's compartments to accomplish a portion of the needed correction. After an undesirably-rotated tooth has initially responded, the remaining correction needed to fully correct the rotated tooth can be achieved by activating the aligner by using Thermoplier® instruments as described. To fully exploit the corrective capacity of an individual aligner, the thermoformed activation features may later be thermo-formed a second time to extend even further into the tooth-receiving compartment. In this manner, a single aligner can serve for multiple progressive treatment phases before being discarded. Progressive activation in this manner serves to counter the decline in corrective force levels resulting from movements as the teeth respond and to help maintain more constant biological forces on the teeth. Bumps serve to focus energy stored locally in the region of the aligner structure adjacent to a bump. The inward-projecting bump causes an outward flexing of the aligner material away from the tooth surface. Configured in this way, bumps gather stored energy from a wider area and impinge that energy onto the tooth at the most mechanically advantageous point to focus corrective forces as needed.

Another family of Thermoplier® instruments has features formed in its beaks that serve to thermo-form an elastic hook feature directly in an otherwise featureless area of an aligner's structure. Elastic hooks are used for connecting orthodontic elastics that provide tractive forces between sectioned portions of an aligner (or an aligner and other fixed structures fixedly attached to the teeth) as needed during treatment FIG. 2 is a detail view of a portion of an aligner 18 showing an area that is been formed into a protrusion or hook 42 to accept an elastic 44. Similarly, other Thermoplier® instruments are used to enhance the performance of aligners by installing other thermoformed features in the polymeric shell.

Another practice used by orthodontists that involves altering a polymeric shell-type aligner beyond its original as-formed configuration is described. The reader is asked to consider the interior, tooth-contacting surfaces of each of the series of tooth-accommodating compartments formed in a typical aligner. As can be appreciated, the inside surface of any one compartment completely surrounds and is in intimate contact with its living tooth when seated. In order for forces such as those that are created through the installation of a single bump to be effective in moving the tooth, the interior wall on the opposite side of the compartment must be relieved or removed to permit the desirable movement of the tooth in that direction. In other words, an axiom for orthodontically moving teeth would state that if a force is applied to move a tooth in a certain desired direction, the tooth will not move in that direction unless free space has first been created for that tooth to move into. To handle such situations, orthodontists may alter aligners by discretely cutting away material to create needed free spaces, or windows. Such windows are created by trimming away aligner material in the direction of desired tooth movement. A window in an aligner will be created, for example, on the labial side of a tooth if a bump is formed on the lingual side. This allows the focused force exerted from the lingual side of the tooth by the bump to avoid an equal but opposite restrictive force, and thus the tooth will in fact move labially into the open window cut out of the aligner on its labial side. Another means for creating free space in this sense is to use one of the Thermoplier® instruments. When heated, the plier can be used to work the area on the labial side of the tooth, still considering the example above. In effect, a bubble can be formed as an outward extending feature of an aligner. When shaped correctly, the space can allow a tooth to move into the free space, but at the same time, provide a stop for the tooth preventing it from moving further than desired and in addition, such a configuration shelters the tooth from unwanted inward pressure of the lips. Sheltering the tooth in this sense further aids in repositioning more labially by removing the lingually-directed forces of the lips.

Another example of relieving an aligner in order to tip a tooth inward or outward (known as correction in terms of torque) follows. Assuming a tooth is essentially in its proper position and only requires uprighting to move into its desired orientation, a window can be cut into an aligner in an area limited to the incisal portion of the tooth. With the installation of a bump at the incisal edge on the lingual side, the incisal edges of the crown will slowly respond by swinging into the relief of the window on the labial. Since in this example, the bulk of the aligner compartment still holds the more gingival portions of the tooth in place, the tooth will be uprighted without any bodily displacement away from its desired position. In this general manner then, orthodontists can create pushing forces on one side of a compartment and discretely relieve the opposite side to very accurately tip, torque, rotate and bodily move the roots of teeth through the supporting alveolar bone. As can be appreciated, aligner-based therapy has to a degree grown into a full treatment modality, not limited to minor correction or finishing functions.

Other methods for exploiting the full treatment potential of polymeric shell aligners are currently being mastered by orthodontists and circulated within the orthodontic literature. Along with the use of Thermoplier® instruments, the relieving of aligners by the creation of windows and the like, and other means for amplifying, regulating, reactivating and extending the corrective force-generating capability of aligners are becoming known. For example, U.S. Pat. No. 6,702,575, "Orthodontic Aligner Auxiliary System," to the present inventor teaches other techniques for extending the usefulness of aligners. The '575 patent involves the installation of separate, auxiliary devices into the physical structure of polymeric shell-type aligners and related methods for preparing aligners to accept and retain such devices. To follow is an explanation of these devices, along with descriptions of how they function and the modifications that must first be installed in aligners so that such devices can function.

The '575 patent involves the introduction of a group of small devices that are intended for strategic attachment to aligners. Such devices are termed "aligner auxiliaries." Prior to installing such devices, a doctor may assess the progress of a case at mid-treatment and in particular, problem areas where the desired response is lagging or particular teeth stubbornly responding to treatment will be targeted. The auxiliaries are installed as required to amplify and focus corrective forces of the aligner to those targeted areas. For example, an auxiliary device known as a "tack" can be installed after a sharply cut hole of a predetermined diameter is pierced through a wall of a tooth-containing compartment of an aligner. The diameter of the hole is slightly less than the diameter of a shank portion of the tack. Next, a tack-installing plier is used to forcibly pop the retentive head of the tack through the hole, resulting in the tight and secure retention of the tack within the aligner structure. The tack pops into position where it is tightly retained in the aligner within the hole. Currently, progressively-sized tacks and other auxiliary devices are commercially available to orthodontists who use them to augment and extend the tooth position correcting forces of aligners.

As can be appreciated, the installation of an auxiliary device such as a tack to achieve the delivery of optimal physiological tooth-moving forces is similar to the effect achieved by installing the bump described earlier. The use of a separate tack however permits the forces delivered to a tooth to be progressively regulated over time by using a sequential series of progressively longer tacks 45 as shown in FIG. 3. In practice, a doctor may adopt a sequential plan where an aligner is initially used as-formed, without any Thermoplier® activations, windows, and tacks or any similar modifications. Such a plain-vanilla aligner may be worn by a patient for two to four weeks for example. At the next scheduled office appointment, the shortest tack (in terms of labial lingual extent) would be installed in the aligner. The conical portion would extend into one of the tooth compartments of the aligner as determined by the clinician. The tack(s) would directly contact and exert force on their respective teeth. The time period between patient appointments is typically adjusted to correspond to a certain degree of tooth movement. At the next appointment, the doctor may remove the short tack, and install a medium-length tack and the short tack would be discarded. As the energy stored in the aligner's structure adjacent to the tack is spent through tooth position correction, a longest of three tacks can be installed after the medium tack is in turn removed and discarded. The present invention anticipates that if given appropriate instruments, patients may be able to install progressive aligner auxiliaries at home according to a doctor's instructions thus avoiding frequent appointments and thereby reducing the overall cost of treatment.

Descriptions of other auxiliary aligner devices and methods for regulating or controllably activating aligners follow. Included in the group of aligner auxiliaries disclosed in the '575 patent is a two-part assembly consisting of a nut with a female thread and an activating screw that threadingly engages the nut. The nut is fixed within the structure of the aligner and the screw passes through the nut inwardly to apply adjustable forces directly to a tooth. Like the tack described above, a nut is installed directly into a precise opening formed in the structure of an aligner. In the case of a nut, a square, rectangular or polygonal-shaped hole is pierced in contrast to a round hole as required by a tack. The square, rectangular or polygonal shape of the hole prohibits the correspondingly-shaped nut from rotating. According to the '575 patent, such a hole can be formed in an aligner using a special plier with a correspondingly shaped and slightly undersized die-punch set formed in its beaks.

Yet another type of auxiliary is retained in an aligner in a manner similar to the tack retention, but it has other labially extending features that serve as an anchor or hook for the attachment of latex or polymeric elastomer bands. As such, this type of auxiliary varies from nuts and tacks in that the hook is not involved in the direct conveyance of corrective forces to an individual tooth. The tractive forces produced by an elastic band attached to such a hook can serve to pull separate portions of an aligner together, or to pull the entire aligner, and the teeth it engages collectively in one direction.

Importantly, while the hook described above must be attached through holes pierced through the aligner, the inward-extending portions of the hook must not contact the underlying tooth. If inadvertent tooth contact occurs, undesirable or unintended tooth movement can result. To prevent such unwanted contact with an underlying tooth, such devices are typically installed in an outset feature formed in an aligner referred to as an "outset land". An example of an outset land 46 is shown in FIGS. 4 and 5. Such features serve as mounting points for non-tooth contacting auxiliaries 45 and can be viewed as a sort of plateau standing out and away from the teeth. The hole 48 for installing any of the non-tooth contacting auxiliary devices is pierced at the center of an outset land 46. The hole 48 serves to retain the auxiliary 45, as shown in FIG. 5, but due to the hole 48 being at a predetermined height above the tooth, undesirable tooth contact between the retaining features of the auxiliary 45 is avoided.

Through locating outset lands 46 at appropriate points around the structure of a polymeric shell aligner 18, other types of auxiliaries can be installed while similarly preventing any undesirable tooth contact. For example, certain auxiliaries can be installed in tandem and can be used to move multiple teeth or groups of teeth apart. Such tandem devices can, for example, support a compressed coil spring and thereby achieve expansion. Such an assembly may span two sections of an aligner where the aligner has been cut into two pieces. An expansion jackscrew is another device that can be supported between devices installed in two outset lands and like the coil spring, they can be used to move multiple teeth or groups of teeth apart.

As can be appreciated from the foregoing, polymeric shell-type orthodontic appliances, like the tooth positioners that preceded them seem to be evolving as needed for ever-wider capabilities. The versatility and usefulness of aligner-based therapy continues to be explored and expanded worldwide. Through the use of aligners first as-is, followed by progressively more aggressive, tooth-specific activations results in patients being treated with a much smaller total number of aligners due to the fact that each aligner can be used progressively before being spent and discarded. A case may require only a few aligners rather than 15 or 20 of them as per current practice. The present invention provides new, improved and automated methods for incorporating all of the various types of modifications required for their expanded role in orthodontic treatment.

Non-Dental Industrial Technologies. Servo and stepper technology provides the basis for much of the automatic or robotic machine movement used in industry today. Essentially, it involves a class of sophisticated electrically-operated motors that contain specially configured magnetic, electrical and microprocessor features enabling them to respond to digital signals rather than standard alternating or direct current as is used to operate standard electric motors.

To describe the sophisticated manner in which these motors operate, a few examples are provided. The armatures of servo motors are capable of steady rotation at exact RPM specifications, or they can speed up or slow down at precise programmed rates. Servo motors can turn at specified rates in either direction and then stop at an angular orientation that is typically accurate to within less than a tenth of a degree. A program command may instruct the armature to turn clockwise 80.625 revolutions and then stop for example. Servo motors are capable of repeatable movements with exact repeatability and high accuracy, with accuracy being maintained regardless of changing mechanical load, inductive load or minor variances in system voltage.

Stepper motors share the capabilities of servo motors but stepper motors exhibit even greater levels of sophistication and have additional capabilities. Stepper motors for example do not only receive and precisely respond to digital signals like servo motors, they also provide various types of digital feed-back to their controlling programs. A stepper motor, in conjunction with its controller can sense changing inductive loads, which can trigger the application of more torque to maintain a constant speed in spite of a varying load. Sensing of changing loads can signal a "stop" once encountering slight resistance for example. A stepper motor can maintain a steady torque in the midst of varying loads and thus accommodate those loads by slowing down or speeding up and as such, can be made to perform in almost any sort of machine motion application. The digital feed-back generated by a stepper motor involves a reporting signal that is sent from the motor back to its controller indicating a variety of exact positioning and load information parameters. It is not incorrect to say that a stepper motor can send back a confirmation that it has responded appropriately to a digital program instruction. Such a return confirmation signal can provide indexing of a master robotic program, allowing a program to proceed on to the next program instruction.

Stepper motors are able to provide digital feedback to their controllers and thus provide digital feedback to a master robotic program through a component called an encoder, which is integrated into the motor's superstructure. It is the utilization of encoder-generated feedback that largely defines the differences between servo motors and stepper motors. It should be noted that encoders, though normally integrated into a stepper motor, can also serve as a stand-alone component of a robotic system such as the present invention. Typically, stand-alone encoders are attached to ends of shafts or other rotary structure to send a positional indicator directly to a master robotic system. In essence, encoders can be considered to be a sophisticated type of sensor, providing digital positional information directly to the master robotic system.

Both servo and stepper motors require a dedicated intermediary microprocessor unit referred to above as a controller, to which they are connected electrically and digitally. Controllers are black-box components that are essentially digitally-controlled solid-state power supplies that serve to regulate the stator and magnetic components within a stepper motor. When incorporated into a larger robotically-operated machine, controllers serve as the link between the master robotic program's digital instructions and the servo and stepper motors that drive actual mechanical motion. Servo and stepper motors are typically attached to reduction gears, rack-and-pinion lineal actuators, worm gear actuators, rotary turntables; cog belts, various types of transmissions, universal-joint-coupled drive shafts and the like. Such actuation systems transmit the precise, digital instructions given to the stepper or servo motor into controlled machine motion.

Sensor Technology. In general, the automation of industrial processes has been directly associated with the development and commercial availability of a rich and varied sensor technology. Advanced sensors see common use in automotive, aerospace, medical, computer and general industrial control systems. The present invention employs an array of sensors to provide various analog and digital trigger and limit signals to the master robotic control program. Like the controller portion of the servo and stepper motors, sensors also trigger and control progression of the master robotic program.

A listing of the types of sensors typically used in automated and robotic systems would include proximity sensors, which are simple electro-magnetic devices that produce a millivolt signal whenever a ferrous mass moves within a certain proximity. Hall effect sensors function similarly to identify the exact position of structure within a set range. Rapid acting thermocouples can provide a millivolt DC current in proportion to temperature. Simple micro-switches can make or break circuits as structures move into desired positions thus preventing further undesirable movement. Micro switches can serve as limit switches for preventing premature movement and crashes between moving and fixed structure. Infrared pyrometers can determine temperature of surfaces from a distance by producing a signal to turn heating power off at certain temperature presets Movement can be terminated when certain machine structures are in desired positions or when they achieve pre-determined force levels after contact. Photocells can actuate a relay switch as a structure makes or breaks the path of a light beam. Various in-line sensors can read and send pressure values within a pneumatic airline or hydraulic system for example. Optical systems based on finely etched glass rods can provide a positional signal typically accurate to within a true positional tolerance of about 0.0001 inch. Importantly, the newest sensor technology involves an array of sensors capable of outputting a digital signal rather than an analog signal. Such sensors are readily integrated into the present master robotic program. Older analog sensors typically produce 0-to-5 volt DC signal or 0-to-12 volt signals, for example, that may have a lineal or exponential relationship to the value being monitored by such an analog sensor. Regardless of the type of sensor, each will generate its own most-appropriate signal gain, and some require their own controllers and dedicated power supplies to interface with the master robotic program.

CAD Software. Computer-aided design or "CAD" software has become a central design and control tool for modern industrial processes and has proven essential in areas such as aerospace and biomedical engineering. CAD software resides on a computer and such a computer then is considered as being a CAD system. Earlier CAD programs were based on a wire frame approach, where new products, machine parts, buildings and objects of all sizes and shapes were modeled by constructing the object element by element as a wire frame, starting with empty virtual space. Modern CAD software is based on a "solids" or solid-modeling approach. Engineers using solid modeling for creating virtual geometry can consider themselves to be starting the design process with an environment completely filled with solid steel or whatever the most appropriate material for the application may be. By selectively removing unneeded surrounding material, the final intended part design emerges. CAD software is readily available from many sources and ranges from freeware available over the internet to large networked CAD systems allowing engineers all over the world to work on a single project.

Important to the understanding of the present invention, the algorithms on which solid modeling CAD software is based result in the virtual CAD solid model being treated as if it were in fact, a true solid part. To better understand this important aspect of solid CAD models, consider the example of a highly detailed, complex part having been designed on a CAD system and complete in the form of a virtual solid model. Through assigning mass properties to the part such as by specifying a specific alloy of steel or aluminum or even a specific species of wood, the CAD system can determine the actual volumetric displacement and therefore weight of an actual part formed from that material with fine accuracy. Further, a center of gravity, a center of mass and a total surface area can be obtained from CAD software. Of particular applicability and conceptual relevance to the present invention, as a CAD-produced virtual model resides in its virtual, orthogonal CAD environment, any given point within that same 3D space can be described as residing in only one of three possible locations. First, such a point can be located outside the external surfaces of the part and therefore separated from it by a discrete distance, or, a point can reside on the surface of the part or, it can reside inside the part. To illustrate this differently, consider a virtual CAD space that contains two parts. The geometric relationships of the two parts can be very accurately handled by the software. Consider for example the parts being moved toward each other. The software can sense the collision as the parts first contact each other. When contact first occurs, the common tangent point of that first contact can be identified. Depending on established parameters, the two parts can careen off in their vector-resultant directions after such a collision. Should conditions be established, the two parts may be allowed to violate each other like a ghost passing through a door. In the case of a violation, the interference volume where the parts extend inside each other can be measured, weighed and isolated. Other parameters may cause the parts to simply stop and lock at the moment of first contact. This ability of CAD systems to handle the geometric relationships of two parts with in virtual space is called "interference detection". All of the foregoing is presented to emphasize the degree with which CAD software treats CAD parts as if they were real physical parts, with particular awareness of the physical boundaries represented by the external surfaces of a part. The various stationary and moving components of the present system can be handled by the CAD software in this manner. A combination of programming accommodating signals from servo and steeper controllers, as well as digital and analog sensors trigger the CAD software to manipulate moving and stationary structure.

CAM Software. Computer-aided machining or "CAM" software is another category of software that operates between CAD software and the post-processor computers found integral to most CNC-controlled (computer numerical control) industrial machine tools. In other words, an engineer may design a part using CAD software and then handle that part in CAM software, preparing it to be automatically machined by a CNC milling machine for example. A CNC milling machine or machining center is such a computer-driven machine tool.

Again, a CAD-designed part file once complete will normally be transferred to CAM software to establish the machining sequence for creating an actual part. Within CAM software, a machinist will plan the sequence of program instructions to be used to robotically machine the part. For example, certain large and aggressive cutting tools will be driven at high feed rates and intermediate spindle speeds to rough-in the part. Roughing-in is a step where the bulk of raw material is removed to allow access to the desired surfaces to be machined by smaller and finer cutting tools. A tool path is just that—the actual path that a machine-driven cutter will follow as it progresses through the material. Multiple cutter tools of various sizes will be taken from the tool changer portion of the CNC machining center and used to machine the final exterior surfaces of a part. If the part has holes, bosses, counter-bores, counter-sinking or threaded holes, each such feature will require corresponding cutting tools. The actual machining will be done according to a step-by-step CAM program that will instruct the machine to proceed according to a certain sequence. The part will then be moved or rotated as required allowing access of the cutters to the areas of the part being machined. Such turning may be accomplished by a servo-driven motor. Typical program instructions issued to the CNC machine tool by the CAM software include instructions to turn off and on coolant spray, to change cutter tools, to set or change cutter tool feed rate, change spindle RPM and so on. All machining operations are performed relative to the surfaces of the CAD model as it has been transferred to the CAM software. A CNC machining center may be connected directly to a CAD/CAM computer, or the CAD/CAM files may be brought to a CNC milling machine on a CD or over the internet.

The foregoing aspects are presented in no particular order, and are intended to convey only the general character and nature of CNC machine programming as it is normally done driven by CAM software. One advanced capability incorporated into CAM software and accomplished on some appropriately equipped machine tools is "visual recognition." An example of how visual recognition functions in a CNC program follows. Consider a tool changer within a CNC machining center. It may hold a dozen or more different cutter tools such as ball-end mills, bottoming-end mills, standard drills of various types and diameters, threading taps, reamers and so on. Since such machines sometimes are operated unattended, and since the part(s) being machined can be destroyed if any of the cutting tools should break, optical recognition is used to inspect each cutter before it touches the part being machined. For this, the programmer will install precautionary steps into a CAM program where a cutter is first taken from the tool changer and positioned so that it can be viewed by a video camera of the CNC machine. The camera will take a series of digital photos of the tool as it is rotated slowly. The features exhibited in the photos will be compared to a retained photo of a new and sharp version of the particular tool. If any of the flutes for example are broken, or if the otherwise sharp cutting edges are seen as worn beyond a certain controlled degree, the machine will signal a stop, or the worn tool can be automatically exchanged for a new or a newly sharpened one. For that, the worn or broken tool will be dropped, and a new tool will be retrieved from the tool changer for use. Alternatively, an alarm may be sounded or a telephone number may be automatically dialed signaling that the machine is in a hold mode until a technician can attend to it. Advanced CAM software driving a modern industrial CNC machining center can be thought of as being a sophisticated robotic machining system. As can be appreciated, appropriate CAM software can be used as a platform for programming any sort of robotic control program. Through the introduction of special programming to an advanced CAM program, a master robotic program can be created such as is central to the present invention.

SUMMARY OF THE INVENTION

This invention provides a robotic system for forming features in orthodontic aligners. A selected region of an aligner is heated above its thermoforming temperature by a heating station (e.g., a laser, hot air pencil, or electrically-heated die). The heated region can then be manipulated by a thermoforming station to create a desired feature in the aligner. A laser station can also be used to trim excess material from the aligner or to cut features into the aligner or create identifying markings.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
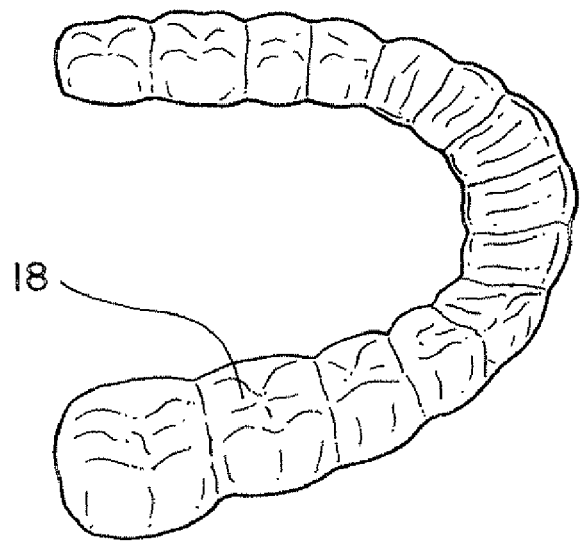
FIG. 1 is a perspective view of a conventional aligner 18.
Figure 2:
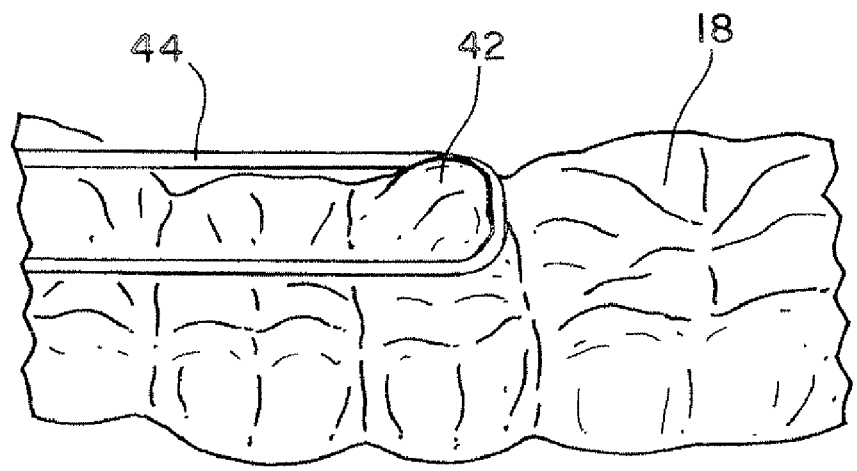
FIG. 2 is a detail view of a portion of an aligner 18 showing an area that is formed into a protrusion or hook 42 to accept an elastic 44.
Figure 3:
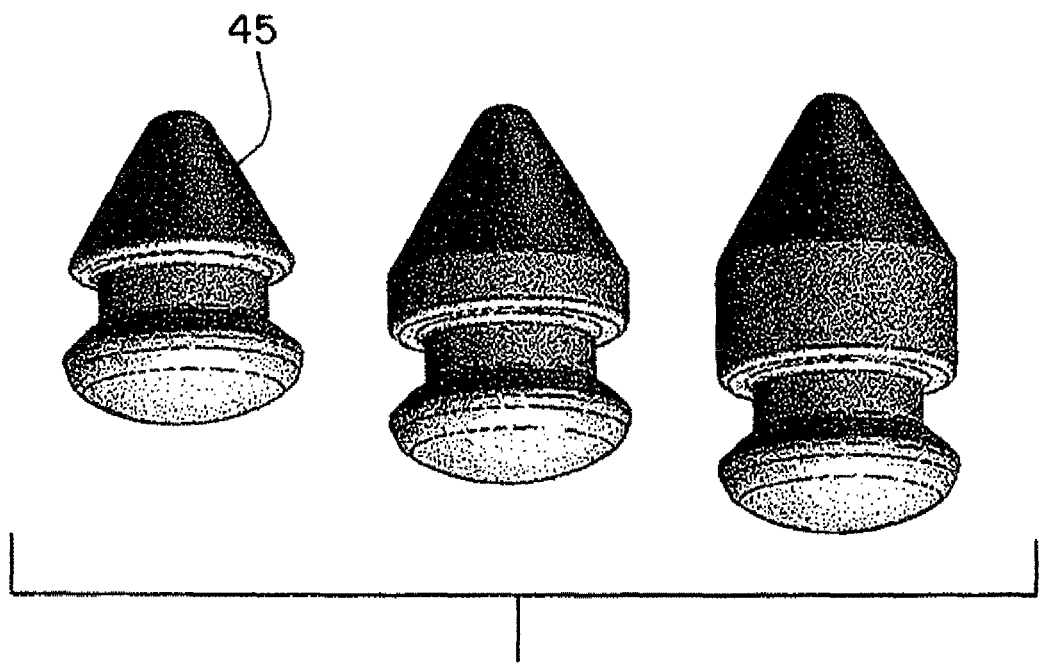
FIG. 3 is a perspective view of a series of progressive aligner auxiliaries 45 referred to as tacks.
Figure 4:
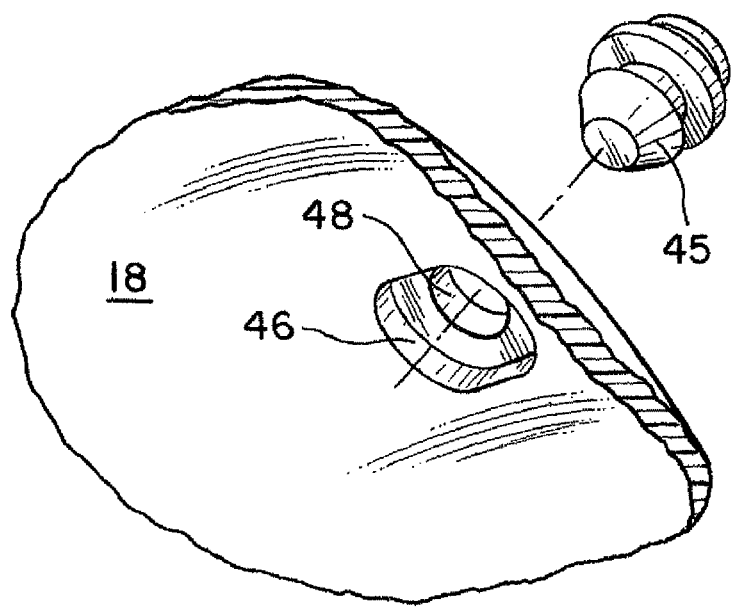
FIG. 4 is a detail perspective view of a portion of an aligner with a raised land and showing insertion of a tack 45.
Figure 5:
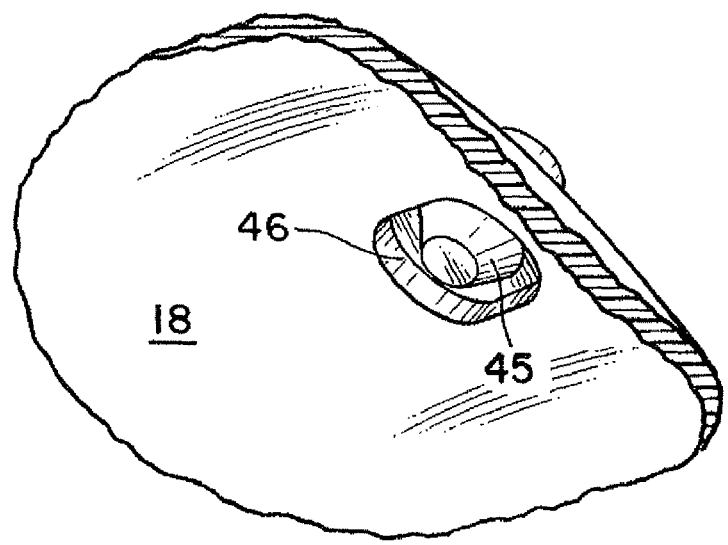
FIG. 5 is detail perspective view corresponding to FIG. 4 after insertion of the tack 45.
Figure 6:
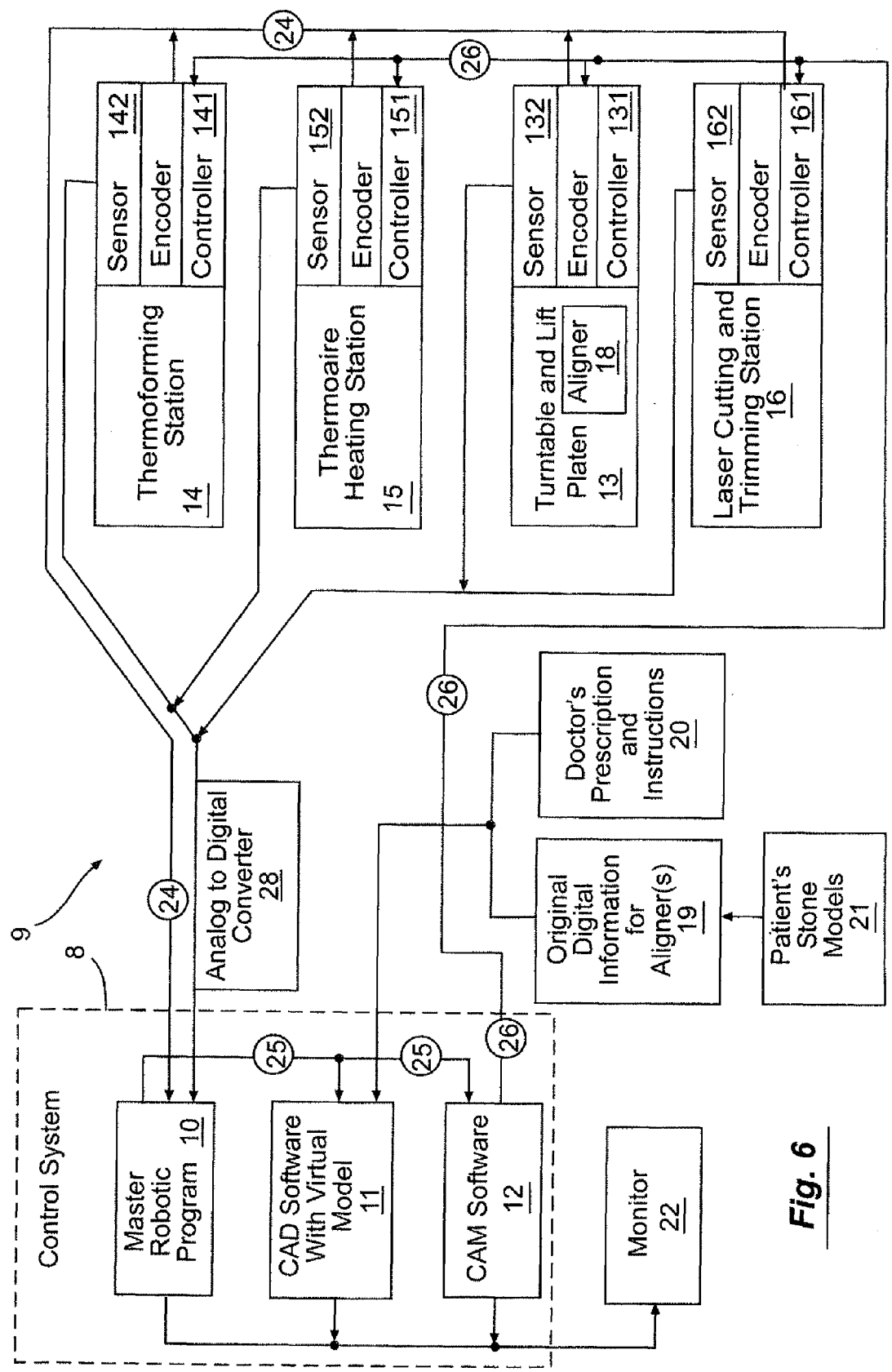
FIG. 6 is a block diagram depicting the system elements used to form aligners according to the present invention.

The present invention provides a robotic system 9 for use in modifying and forming features in conventional polymeric shell aligners. A block diagram of the present system is shown in FIG. 6. The major mechanical components of the robotic system 9 are a centrally-located turntable and lift platen 13 that provides three-dimensional positioning of an aligner 18, and a number of robotic stations 14, 15, and 16 arranged about the platen 13 for performing actions to form features on the aligner 18 and to trim away excess material. All of these mechanical components are under the control of a control system 8. For example, the stations can include at least one heating station 15, 16 for heating a selected small region of an aligner above the thermoforming temperature of the aligner material, and at least one thermoforming station 14 for manipulating the heated region to form a desired feature in the aligner 18. The control system 8 is typically implemented on a conventional computer with a processor, memory, and data storage (e.g., hard disk). The control system 8 is also equipped with a master robotic program 10 controlling operation of the mechanical components of the present system, as well as CAD software 11 and CAM software 12.

It should be noted that the robotic system 9 consists of various integrated systems that can all be used and supported within a commercial dental laboratory infrastructure. The robotic system 9 would typically require dedicated single-phase electrical service, a compressed air source, and a high-speed internet connection. Operation of the machine can be managed by a technician with CAD experience, CNC/CAM programming experience and general computer skills along with a knowledge of orthodontic laboratory materials and procedures. Operation of the robotic system 9 is directed toward processing a single aligner-type orthodontic appliance 18 or a series of such appliances for an individual orthodontic case. Multiple aligners are custom-processed sequentially, one at a time according to instructions 20 supplied by a patient's orthodontist according to the needs of a single individual. The attending orthodontist provides various types of information and instructions 20 relating to the particular patient's diagnosis, treatment objectives and treatment plan. The doctor's instructions 20 are followed by the technician while processing the patient's aligner(s) 18.

The present invention requires that a polymeric shell-type aligner 18 be positioned and held within the robotic system 9 for processing. In the embodiment shown in the accompanying drawings, the aligner 18 held on a turntable and lift platen 13 that enables the robotic system 9 to position and rotate the aligner 18 in three-dimensional space relative to the heating and forming stations 14-16. It should be understood that any type of servo-controlled turntable or work support platform for positioning an aligner 18 should be considered to be a "platen" within the scope of this invention.

Provision of an aligner 18 or a series of a patient's aligners can be accomplished by providing pre-manufactured standard aligners for further processing according to the present invention. Additional digital information would be required to process such a case. The original digital code 19 used to grow the series of rapid prototype-produced thermo-forming patterns over which the subject aligners were formed can be provided. Such digital code 19 would typically be provided as an .STL file-type, or other common digital file type for loading into the CAD software 11 of the present robotic system 9. The digital code 19 may be delivered via the internet directly to the CAD software 11 or presented to the technician on a compact disk (CD) or any other transportable digital storage medium. Alternatively, digital code representing virtual models of the aligners themselves may be provided, or generated by 3D scanning of an actual aligner.

As another alternative, stone models 21 of the patient's upper and lower occlusion and soft tissues may be provided to a commercial dental laboratory. As separate steps unrelated to the present invention, such stone models 21 can be scanned and a complete set of standard aligners 18 can be fabricated in a conventional manner and made ready for processing using the present system. By fabricating the aligners in that conventional manner, both the actual aligners 18 created and the associated CAD code 19 would be available for further use within the present system. The foregoing relationships between steps used to fabricate conventional aligners, and the steps required to further process those aligners in the present system are provided to highlight the integratable nature of the present system with the conventional aligner fabrication process. Given that, the present invention may be seen as being most efficiently operated in-line, following seamlessly in a data-sharing mode with the standard aligner fabrication process covered earlier. In such a case, there is a group of features that can be virtually installed in the otherwise standard aligners during the virtual CAD portion of the standard aligner fabrication process. Such features prepare aligners for the expanded capabilities covered earlier including the accommodation of aligner auxiliaries and other features such as outset lands and other passive and active outset or inset features, markers, datums and the like. The present invention includes the installation of such passive, active and auxiliary accommodating features as virtual features to be incorporated into the virtual model 11 of the present system or as an adjunct to a conventional aligner-forming process.

To illustrate a preferred processing sequence involving a typical case according to the present invention, the role of the CAD technician is described. The CAD technician working within the orthodontic laboratory first receives the patients virtual (digital) models 19, a completed prescription form and other instructions 20 for aligner-type appliances needed by the orthodontic patient, all of which are sent in by the patient's orthodontist. The materials provided by the orthodontist in the example to follow relate to a series of nine progressive aligners that are needed to treat a patient's misaligned teeth. The technician sees that the prescription and instructions 20 from the orthodontist outline a treatment plan that breaks the nine aligners into three groups of three aligners as depicted below:

|  | No Activation | Moderate Activation | Maximum Activation |
| --- | --- | --- | --- |
| Group 1 | x | x | x |
| Group 2 | x | x | x |
| Group 3 | x | x | x |

From the instructions 20, provided, the technician understands that the orthodontist's treatment plan calls for a total of nine progressive aligners to be configured according to the schedule above.

Considering only the three aligners listed in the "No Activation" column, the technician understands that the doctor will use those aligners in a plain-vanilla or in an as-is configuration. Correction achieved by the aligners in the "No Activation" column will result only from the positional biasing of the tooth-receiving compartments as described earlier. As such, the technician will not process those three aligners any further. For the aligners listed in the "Moderate Activation" and "Maximum Activation" columns, the technician will activate and modify those aligners using the present robotic system 9. The No Activation, Moderate and Maximum Activation aligners are all sequential. In other words, within each group, the Moderate Activation aligners are intended to take over tooth-moving functions at the point where the "No Activation" aligners left off, moving the teeth incrementally further along the intended movements. Each of the three "Maximum Activation" aligners will similarly take over at the point that the preceding intermediate activation aligners left off, again moving the teeth further, generally to the maximum range possible within the physical limits of the particular aligner. Stated differently, the group 1 "Maximum Activation" aligner is configured to hand-off tooth-moving progress to the group 2 series and so on. In further assessing the doctor's prescription 20, the technician may see that he or she will be provided with three identical aligners of a group 1 configuration, three identical aligners of the group 2 configuration and likewise, three of the group 3 configuration. Since the "No Activation" aligners are intended to worn as-is, the technician sees that processing according to the present invention will be limited to only six of the nine aligners.

Ultimately then, the orthodontic patient will receive instructions from the orthodontist to wear the series of aligners in this sequence:
 1, No Activation
 1, Moderate Activation
 1, Maximum Activation
 2, No Activation
 2, Moderate Activation
 2, Maximum Activation
 3, No Activation
 3, Moderate Activation
 3, Maximum Activation The nine aligner-type appliances 18 needed for the particular case cited in the example above may be provided to the technician in any one of these general ways.

In addition to the prescription information 20 and other instructions, the attending orthodontist may provide a fully-fabricated series of physical aligners submitted for processing according to the present invention. As can be appreciated, in order for that existing set of aligners to be processed according to the present invention, the orthodontist must also provide the technician with the digital CAD code 19 originally used to conventionally form the aligners. When provided, that data will reside in the CAD software 11 of the present system.

In addition to the prescription information 20 and other instructions, the orthodontist may forward only the patient's set of study models 21 to the orthodontic laboratory. In such a case, the set of nine aligners must be fabricated, beginning with the step of scanning the patient's stone models 21, followed by the steps of virtual correction, rapid prototyping and thermo-forming. All of these steps were described earlier. In such a situation, during the CAD phase involved in the fabrication of the series, certain types of features accommodative of aligner auxiliaries and other inward or outward extending passive or active features may be installed within the various aligners' solid virtual structure according to the present invention.

As yet another possible path for the technician to configure the case, the orthodontist may supply CAD data representative of the patient's occlusion produced by in-office scanning of the patient's teeth, or in-office scanning of the patient's models, or a CAT scan of the soft impressions taken of the patient's teeth. In such a case, that information will serve in lieu of the original digital information 19 and will reside in the CAD software 11.

To gain an understanding of robotic motion as well as to gain an understanding of the robotic functioning of the present invention, the reader is directed to consider: (a) the relationship between CAD/CAM software and servo/stepper technologies; (b) the nature of robotic programming where the completion of each program step requires that certain parameters be achieved, or certain conditions be met, before the program can advance to the next program instruction; and (c) the dual-nature of the positioning and motion of the various machine components along with the aligner itself and the fact that all such positioning and motion is duplicated virtually within the CAD virtual model 11 as signaled by the master robotic program 10 as it actually occurs. In other words, an observer would see actual motion of the aligner 18 and robotic components 13, 14, 15, and 16, and also see the same motions replicated on the computer's monitor 22.

As described earlier, the defining characteristic of stepper motors is the capacity for generating sophisticated types of digital feedback 24 as they respond to digital instructions 26 from the CAM software 12. That feedback 24 is sensed by the stepper motor's various controllers 131, 141, 151, and 161 associated with the platen 13 and robotic stations 14, 15 and 16, as shown in FIG. 6. The feedback compiled by the various stepper motors that function within the platen 13 and robotic stations 14, 15 and 16 is transferred from the corresponding controller 131, 141, 151, and 161 to a master robotic program 10 residing along with the CAD/CAM software 11, 12 in the control system 8. The various types of stepper motor feedback signals 24 sent to the master robotic program 10 typically include binary yes/no signals.

As an example of how such signals impact the robotic operation of the system, the following description is provided. Thermoforming dies included within the thermoforming station 14 of the robotic system 9 would typically be in their retracted position before the thermoforming servo can advance. The servo motors involved with advancing and retracting the thermo-forming dies must usually first send a confirming signal that they have in fact rotated the thermo-forming dies to their retracted position before the thermo-forming servo can advance. Once such a confirming signal 24 is received by the master robotic program 10, several things occur. For one, the master robotic program 10 can advance to the next sequential program step. Also, a confirmation is sent to the CAD software 11 and the CAM or CNC software 12 by a triggering signal 25. Another particular program step may be configured as a binary "if yes go; if no stop"-logic associated with it and only a "yes" allows the master robotic program 10 pointer to advance, which is similarly coordinated with the CAD/CAM software 11, 12 by a triggering signal 25. Also occurring after such a confirmation, the CAD software 11 maintaining dynamic virtual model of all system movement will use that same stepper feedback "yes" to trigger spreadsheet-driven dynamic motion commands within the CAD software 11. Such a triggering signal 25 can drive spreadsheet-driven instructions and spreadsheet-driven updating of the CAD virtual model 11. Spreadsheet-driven instructions and spreadsheet-driven updating are part of a known methodology incorporated into CAD software 11, especially if it is operating within a Microsoft Windows environment. For example, the CAD software can interface with Microsoft Excel spreadsheets. Values derived by the spreadsheets are inserted as dimensional, angular or special values within individual sketches that constantly rebuild the parts of assemblies. Virtual parts such as the entire virtual machine and virtual aligner 18 can be altered according to numbered rows of conditional sets or value sets established in multiple, vast Excel spreadsheets that are set up to relationally interface with CAD software 11. Further, the values themselves within the spreadsheet rows and columns can be variably generated "live": from actual stepper/sensor feedback values 24. Returning to the example above, the sensor feedback 24 from the stepper and servo motors, as compiled by their various controllers 131, 141, 151 and 161 serve to allow the precise rotation of the virtual thermoforming dies into their operating positions within the CAD virtual model 11. The system operates as if cognizant of exactly where the target surface of the aligner 18 is positioned in 3D space within the orthogonal space of the robotic system 9. A significant portion of the spatial cognition can be achieved through collision detection and detection of the special relationships between surfaces of parts of the CAD assembly. Once in forming position, the geometric relationships between the positions of the actual machine components within the thermoforming station 14 and the aligner 18 are replicated within the CAD environment 11 from spreadsheet values and can be seen on the computer monitor 22. In this manner then, the master robotic program 10 advances, and the virtual CAD model 11 of system activity is maintained, synchronized with the actual robotic activities. The position of the aligner 18 and the various aligner-modifying tools 14, 15 and 16 are all known, monitored and maintained in 3D space in this manner allowing the relationships of the CAD-generated virtual elements to move in lock-step with the actual elements.

The CAD system 11 is also tied to the master robotic program 10 and similar program advancing or program hold commands 25 can emanate from within the CAD software, back to the master robotic program. Such signals 25 act similarly to hold or advance the program pointer of the master robotic program 10. For an example of how the CAD activity impacts the master robotic program, a servo system advancing thermoforming dies within the thermoforming station 14 toward a target point on an aligner 18 causes the CAD system 11 to mimic this activity virtually in response to servo-generated positional feedback 24, acting directly with the CAD software 11. As the virtual thermoforming die approaches the virtual aligner, the "interference detection" capability of the CAD software 11 will sense the moment the thermoforming die within the thermoforming station 14 makes contact with the surface of the aligner 18. Once that happens, the CAD software, sensing a collision can trigger a "stop" command 26 to the controller 141 of the servo system for the thermoforming station 14. Alternatively, the thermoforming die within the thermoforming station 14 may stop moving closer once it reaches a certain proximity to the aligner 18 target surface even through no virtual collision has occurred. All such geometric relationships can be monitored by the CAD software 11 and as predetermined conditions are met, the CAD software 11 can signal both the master robotic program 10 and the servo-driving CAM software 12 accordingly through a triggering loop 25.

The feedback from various types of sensors 132, 142, 152 and 162 shown in FIG. 6 also serve to drive the master robotic program 10 from one program instruction to the next by similarly providing conditional binary information and other types of analog or digital signals. Whn a particular signal value meets a preset signal value, the program will advance. Other sensors within the present system can serve in closed-loop applications without interfacing with the master robotic program 10 at all. For example, the thermoforming dies of the thermoforming station 14 must function only within a certain temperature range. For example, an infrared pyrometer-type sensor or standard thermocouple-type sensor can serve to monitor the temperature of the thermoforming dies independently from all other system functions. If the temperature drops below a low limit, the infrared pyrometer triggers a relay that sends heating current to the dies and conversely, once the temperature reaches a high limit, the current is turned off. Again, this is an example of sensors operating within the robotic system 9 but outside of the master robotic program 10 or triggering loop 25. Simple limit switches and proximity-type sensors can operate both in conjunction with the master robotic program 10 or, if appropriate, independently in various closed-loop functions throughout the robotic system 9.

Platen. One embodiment of a servo-activated turntable and lift platen 13 is shown in FIGS. 7 and 9-11. In FIG. 11, a conventionally-formed, but untrimmed aligner 18 is mounted on the datum posts 135. The turntable 134 and its related positioning mechanisms represent a subsystem of the current invention that is completely stepper and servo driven. It serves to position any point on the labial, buccal or lingual surfaces of the tooth compartments of an aligner 18 into orthogonal relationship with the x, y, z datums of the other robotic stations 14, 15 and 16. To describe this portion of the robotic system 9, the servo-activated turntable 134 employs a vertical post portion. Attached to the vertical post is a servo-driven, rack-and-pinion gear assembly 138, 139 capable of raising or lowering the entire platen structure holding an aligner 18. The turntable 134 supporting the table 133 accomplishes servo-positioning of the aligner 18 in terms of 360° rotation about a vertical z-axis. The accuracy of such positioning can be maintained with an accuracy of a fraction of a degree using standard industrial components. The spherical portion above the rotating portion of the turntable 134 is capable of establishing a precise declination of the table 133 and aligner 18 by tilting them. As can be appreciated, in combination, the multi-axis servo-positioning system described is capable of transposing a target point designated for alteration within a true position relative to the orthogonal coordinate systems of each of the robotic stations 14, 15 and 16. The various servo systems can all operate as if integrated into one recumbent coordinate system even though each is clocked 90° to the rest in the example depicted by the figures.

After the suck-down step when forming an aligner 18, excess material often remains around the periphery, which is a remnant of the flat sheet material from which it is formed. A first step in further processing a conventional aligner involves trimming away of such excess material, if present. According to the present invention, the untrimmed aligner is mounted on three datum posts 135 extending from the table 133 of the platen 13. One method for holding and immobilizing the aligner 18 on the datum posts is by a deep vacuum drawn through hollow datum posts 135. Other embodiments may utilize three additional corresponding posts similarly extending from above the aligner 18 in apposition to the three datum posts 135 shown in the drawings, thus mechanically clamping the aligner 18 in place. Precise positioning of the aligner 18 in a predetermined orientation on the platen 13 is required for the precise functioning of the entire robotic system 9. Because of that requirement, predetermined registration points or mounting points are preferably located on the surface of the aligner. These points may be standardized as the occlusal-most extent of the mesial buccal cusps of the first molars and at the mid-mesial/distal point along the incisal edge of the left central tooth compartment for example. The registration points can be formed into the virtual CAD solid model 11 of the aligner during initial fabrication and may be formed as very small, sharp, inward-projecting cone-shaped features sized to form sharply according to the thickness of the aligner material.

Figure 10:
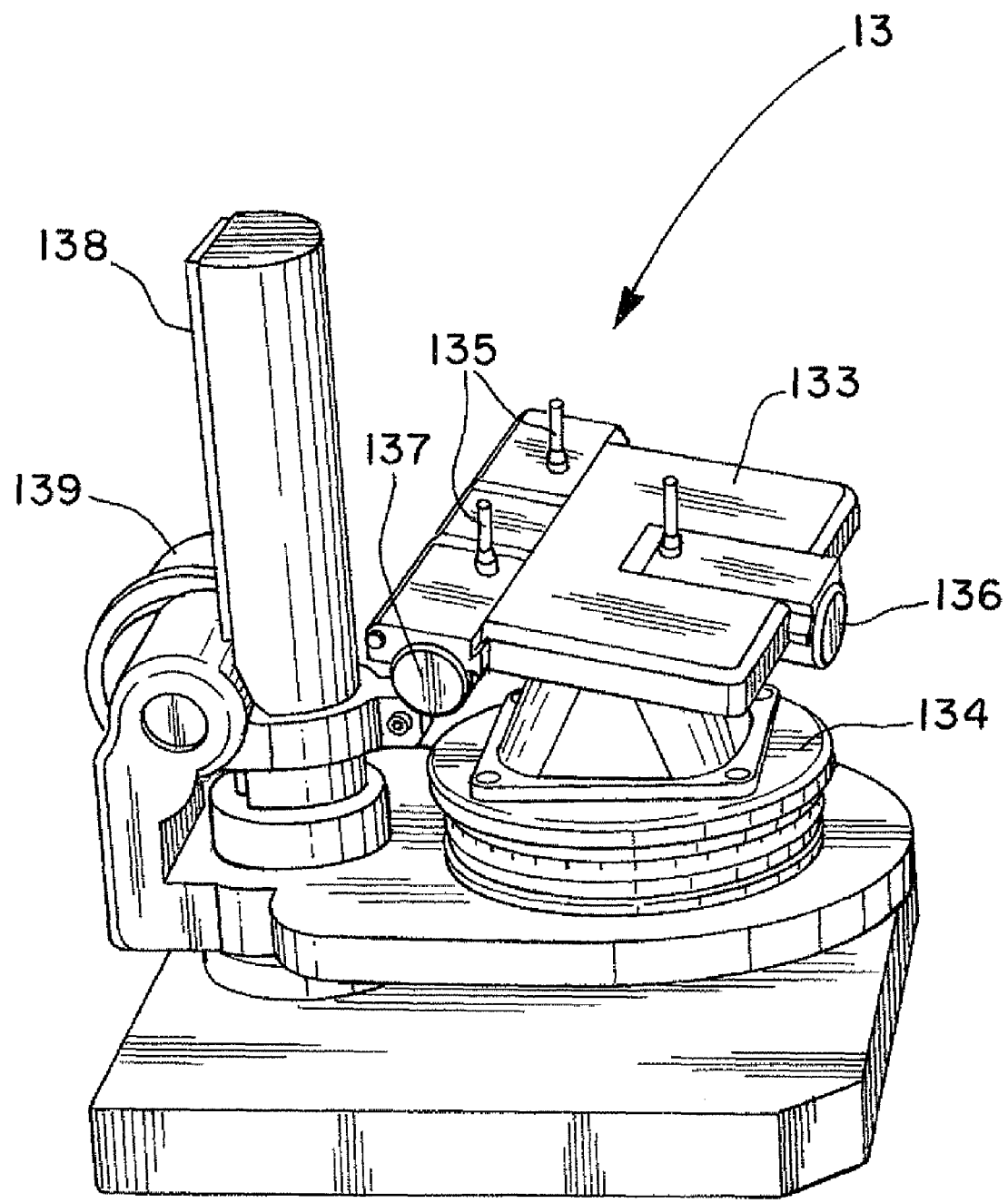
FIG. 10 is another detail perspective view of the turntable and lift platen 13 corresponding to FIG. 9.
Figure 11:
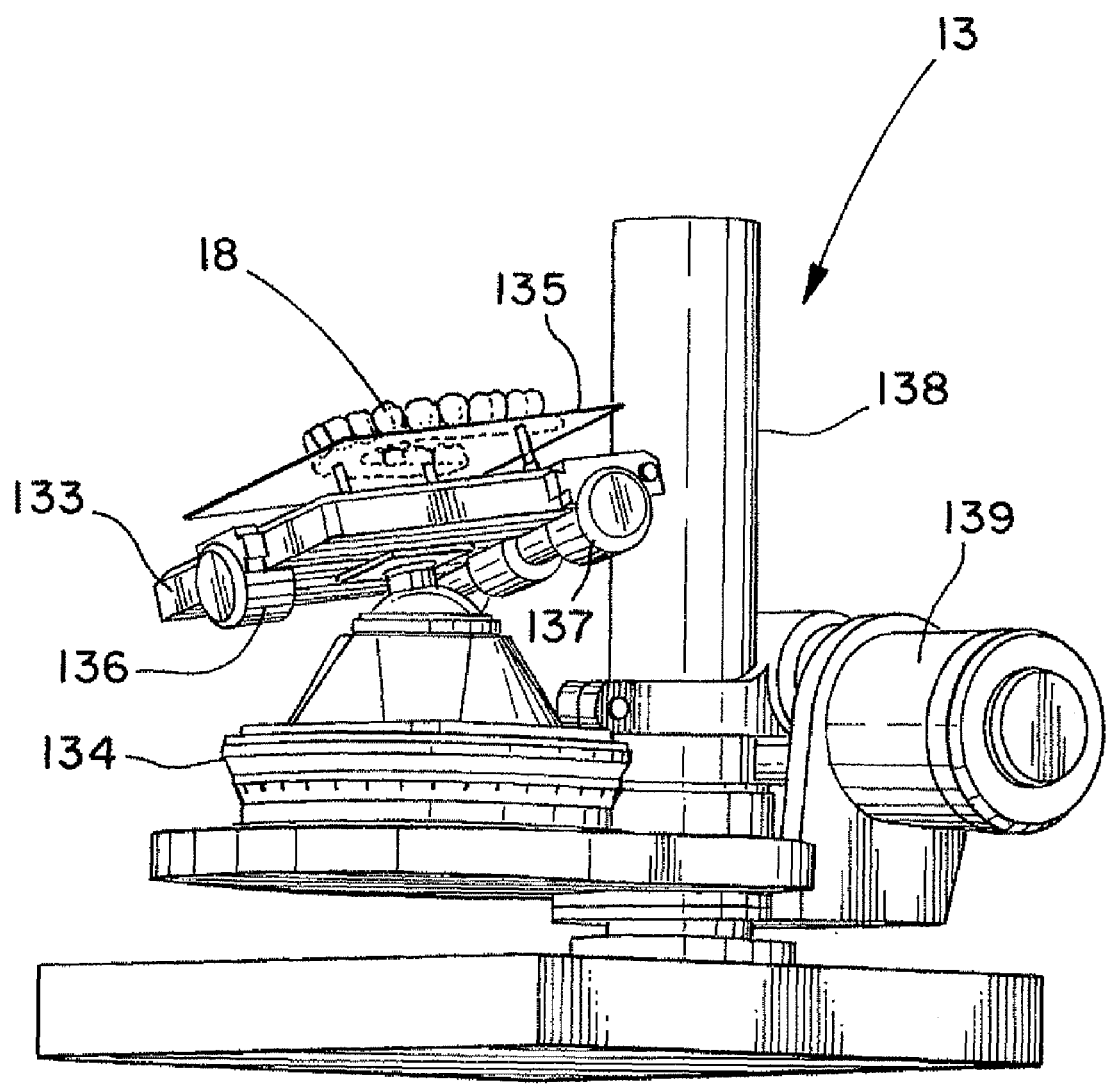
FIG. 11 is yet another detail perspective view of the turntable and lift platen 13 holding an aligner 18 being processed.

Looking closely at the rendering of the platen 13 in FIG. 10 and its datum posts 135, which serve as aligner mounting points, it can be seen that the positions of the two posterior points can be adjusted by means of transverse-positioning servos 137, so that these posts can move independently inward or outward (transversely) from the midline of the aligner. This is to allow the datum posts to position themselves directly in register with the molar registration points of the aligner described immediately above. The location of the single anterior datum post is similarly adjusted by a servo 136, but perpendicular to the others in a mesial-distal axis along or parallel to the saggital mid-line of the aligner. A servo-driven aligner mounting system is thus provided allowing the servos 136, 137 driving the datum posts 135 to pre-position the posts so that their vacuum orifices fall in direct register with the registration points preferably pre-formed into the subject aligner 18. The vacuum orifices located atop the datum posts 135 can be countersunk to accommodate the small downward extending cone shape of the formed registration points so that a deep vacuum rigidly holds the aligner oriented according to the beginning positional assumptions of the virtual CAD model 11. The present invention anticipates that the transverse positioning of the posterior datum posts, combined with the anterior-posterior positioning of the anterior datum post alone may not be capable of capturing all aligners by their mesial buccal first molar cusps and a third point midway along the incisal edge of a left central. However, the registration points preferably installed during aligner fabrication can be located in accordance with such constraints, allowing the system to position the three datum posts so as to be able to mount any aligner, regardless of degree of asymmetry of the dental arch they reflect. A step in processing an aligner 18 then would be the auto-positioning on the three datum posts 135 precisely in position to accept the aligner. After that is accomplished, the aligner drops on to the datum posts 135 in precise registration with the known coordinates of the robotic system 9.

Figure 12:
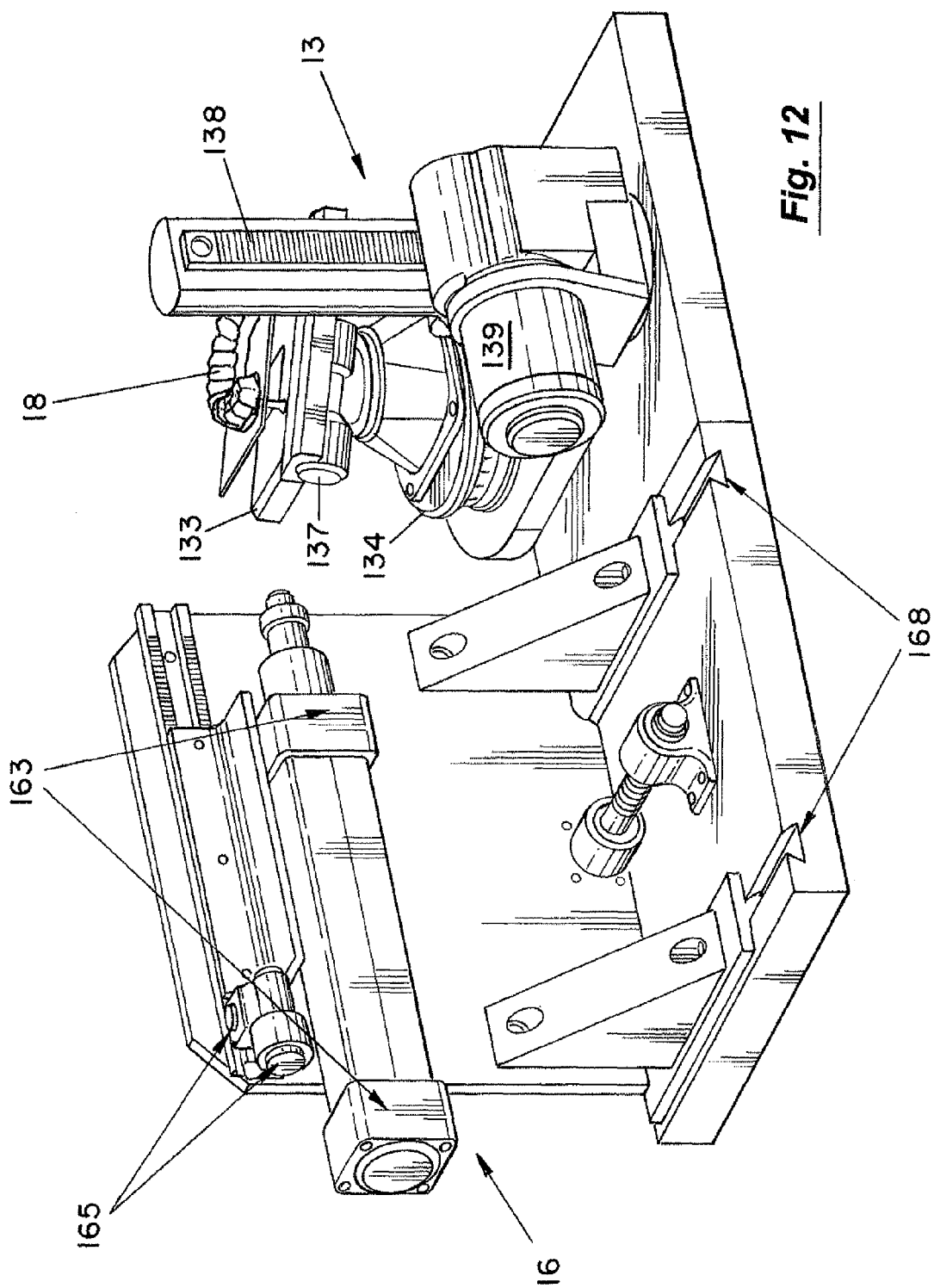
FIG. 12 is a detail perspective view of the laser cutting and trimming station 16 and the turntable and lift platen 13.

Laser-Cuffing Station. A detail perspective view of the laser cutting and trimming station 16 is shown in FIG. 12. The first step in the aligner processing sequence is to trim the aligner 18, unless the aligner was trimmed during a conventional fabrication process. Trimming not only involves trimming away of the remnants of the sheet material from which the aligner is formed, it also involves cutting the material away in a festooned or scalloped manner following the gingival margin of the teeth around both the buccal/labial and lingual gum line. A step taken by the CAD technician managing the manipulation of the original solid model will be to virtually trim the model as required. The CAM programming phase of the current invention orients the coordinate system of the laser-cutting station 16 in contiguous relation with the coordinates of the platen 13. Its orientation is clocked 90° to the platen 13. This is accomplished through a combination of transposing axis values: the laser 163 moving back and forth in the X-axis according to motion generated by the X-positioning stepper motor 165 and the Y-positioning servo 167 in tracks 168, along with Z-axis motion generated by the lift servo 139 of the platen 13. In addition, orientation and position of the table 133 of the platen 13 can be changed by the servo-driven turntable 134 and rack-and-pinion elevation mechanism 138, 139 of the platen 13, as previously discussed.

A smooth, articulated relationship will be maintained between the laser beam and the aligner trim path established across the surfaces of the aligner. The smooth and synchronized movements of the various servo and stepper motors working in concert involve simultaneous raising and lowering of the aligner while it is tipped and rotated, along with the laser heard moving inward and outward from the center of the machine, maintaining a constant focal length between the aligner and the laser head. Descriptions of other functions involving laser energy follow.

As described earlier, there are a number of reasons to perforate an aligner 18, forming various types of holes. For example, a window involves the cutting away of material to form an irregular-shaped hole in the aligner structure. Such holes may have a complete periphery or they may overlap onto the trimmed edge of the aligner and thus appear as a notch. The insertion of tacks requires precise, small, round holes to be cut with controlled diameters in the 0.050 to 0.065 in. range. Other types of precise round, square and non-Cartesian holes can be installed, including holes in outset lands. All such holes are cut cleanly by laser energy through multi-server/stepper orchestration by the master robotic program 10 as driven by the CAM software 12, with paths determined by the CAD software 11. Laser energy impinging on the polymeric shell of the aligner produces a cutting edge that is polished and without carbonization of the polymer when the energy and the feed rate are set optimally. Tolerances for true position and configuring such holes can be held to within 0.0015-inch. An absorbere, rigged to follow the laser head, can be inserted within the trough of the aligner to prevent damage to adjacent portions of the aligner being processed.

Aligners often require identification markings. For example, a series of aligners needs a serial number indicating the sequence in which they are to be worn by the patient. Other markings such as patient number, case number, doctor number, material type and thickness, and any other requirements for alpha-numeric symbols can be installed by the laser at the same time the cutting and trimming is accomplished. Such markings do not necessarily need to completely pierce the material, and as such, such markings could be considered "laser etching" of the material. Laser etching may be sufficient to install permanent alphanumeric characters. In such a case, the master robotic program 10 in combination with the CAM software 12 would act together to alter laser power to an appropriately lower value and higher feed rate of the laser beam as it travels across the surface of the aligner material. A slightly out-of-focus setting for the laser in terms of focal length may also aid in regulating laser energy for laser etching. The actual path for creation of the alphanumeric characters would be handled by the CAD/CAM technician during the CNC programming stage.

Figure 13:
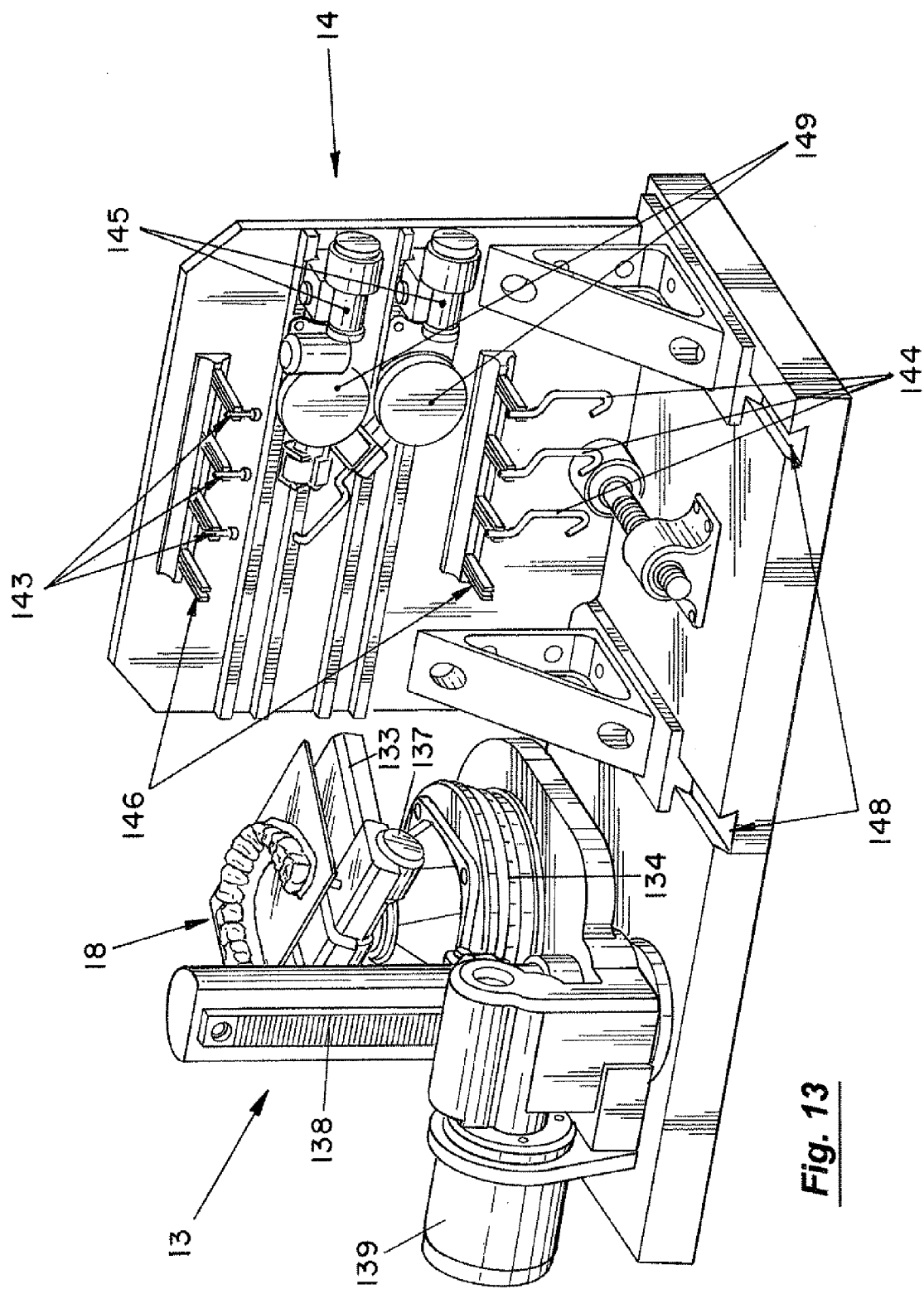
FIG. 13 is a detail perspective view of the thermoforming station 14 and the turntable and lift platen 13.

Thermoforming Station. A detail perspective view of the thermo-forming station 14 is shown in FIG. 13. The thermoforming station 14 is preferably positioned to the side of the platen 13, opposite the laser cutting station 16. Its orientation is clocked 90.degree. to the platen 13. Through a combination of rotation, lifting and tilting of the aligner as it is precisely held by the mounting posts 135 of the platen 13, and along with movement of the entire thermoforming station 14 in the y-axis, any point on the labial, buccal and lingual surfaces of the aligner 18 can be positioned perpendicularly to the axis of advancement of the thermoforming dies manipulated by the thermoforming station 14. Once the excess aligner material is trimmed away by laser cutting as described, the inner thermoforming die 144 can approach the aligner and swing up into forming position on the inside of the trough formed by the series of tooth receiving compartments of the aligner 18. The outer thermoforming die 143 can approach the inner die along the same axis, trapping and forming the aligner structure caught in between. In this manner, bumps, bubbles, outset lands and the like can be thermoformed into the aligner 18 according to the master robotic program 10 as orchestrated by the CAM software 12 as virtually modeled by the CAD software 11 of the control system 8. Multiple pairs of co-working thermoforming dies 143, 144 reside in the upper and lower tool changers 146 of the thermo-forming station 14 and are held until needed as per instructions from the master robotic program 10 of the control system 8. Alternatively, some types of features can be formed in the aligner using a single thermoforming die. The thermoforming dies can be heated with standard thermocouple-controlled resistance heating elements and/or the thermoforming dies can be heated using a small stream of hot air supplied by a THERMOAIRE localized heater pencil 153 as the heat source, as described below.

In the embodiment of the thermoforming station 14 shown in the accompanying drawings, the Y-axis position of the thermoforming dies 143, 144 is controlled by a stepper motor 147 (see FIG. 8) that causes the thermoforming station 14 to slide in a series of tracks 148 in the base of the station. The thermoforming dies 143, 144 are extended and retracted along the X-axis by two rack-and-pinion mechanisms driven by stepper motors 145. The thermoforming dies 143, 144 are held by rotary servos 149 that can be controlled to raise and lower the tips of the dies.

Figure 14:
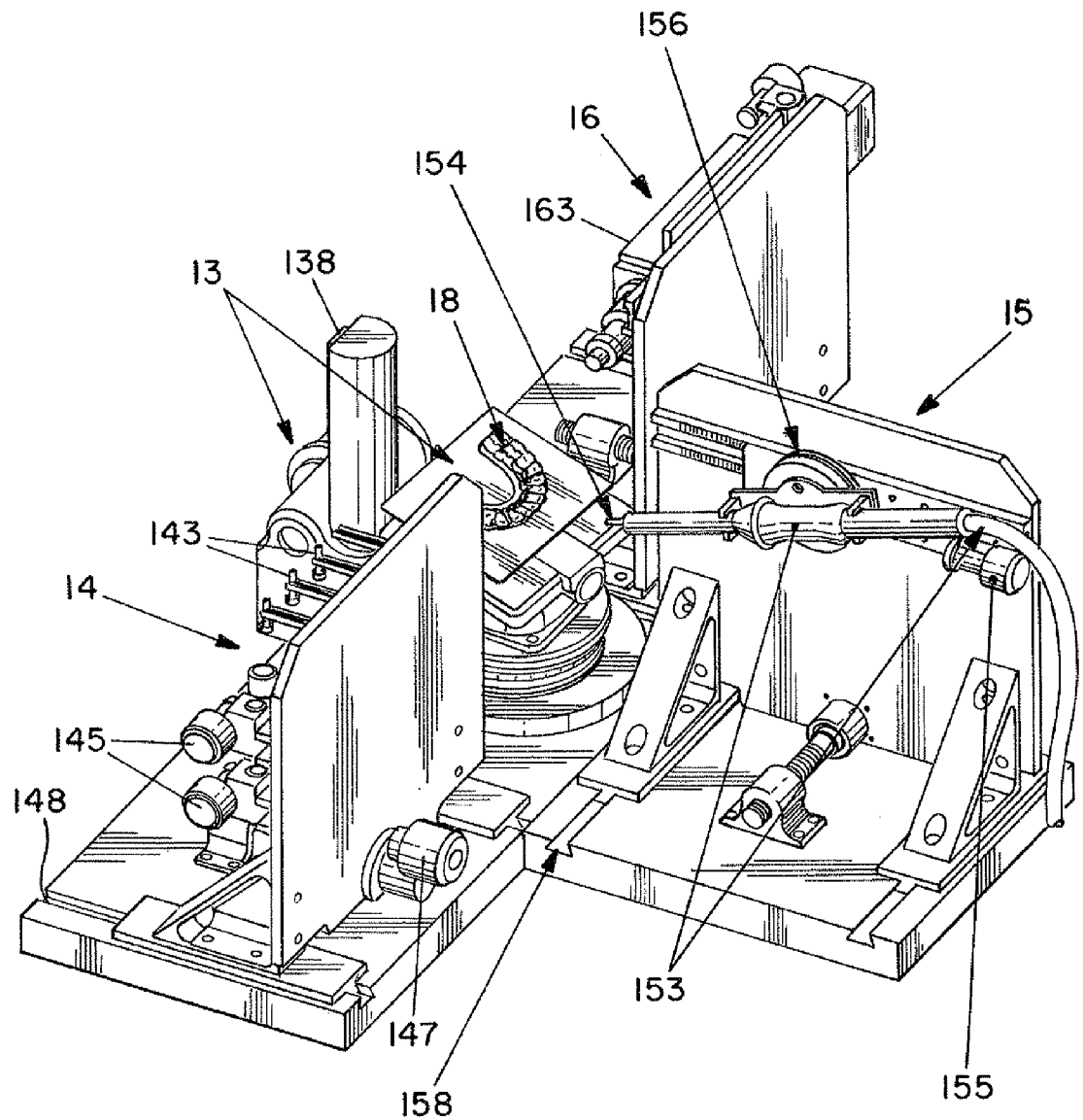
FIG. 14 is a detail perspective view of the THERMOAIRE localized heater station 15 and the turntable and lift platen 13.

THERMOAIRE localized heater Heating Station. Directly in front of the platen 13, and preferably perpendicular to the thermoforming and laser-cutting stations 14 and 16 is the THERMOAIRE localized heater heating station 15 FIG. 14 is a detail perspective view of the THERMOAIRE localized heater heating station 15. It functions to direct a concentrated flow of super-heated air to localized areas of the aligner 18. Such areas may measure only a few millimeters in extent, and are heated to predetermined temperatures ranging from 325° F. to 525° F. The region of the aligner pre-targeted for heating is positioned in front of the tip 154 of the THERMOAIRE localized heater pencil 153 through a combination of servos controlled by the control system 8. In particular, the X-axis position of the entire THERMOAIRE localized heater heating station 15 is controlled by a servo 157 and tracks 158. The Y-axis position of the THERMOAIRE localized heater pencil is controlled by a rack-and-pinion mechanism driven by servo 155. The elevation of the THERMOAIRE localized heater pencil tip 154 can also be adjusted by a vertically-mounted servo-driven turntable 156 shown in FIG. 14. Once the target region is heated, the turntable 134 of the platen 13 quickly rotates 90° to orient the aligner 18 toward the thermoforming station 14. There, the tool holder(s) pick-up the appropriate thermoforming die(s) and bring the thermoforming die(s) into forced contact with the aligner 18. As the target region of the aligner cools, the thermoformed configuration resulting from contact with the forming die(s) becomes a permanently formed feature in the aligner's structure.

Figure 15:
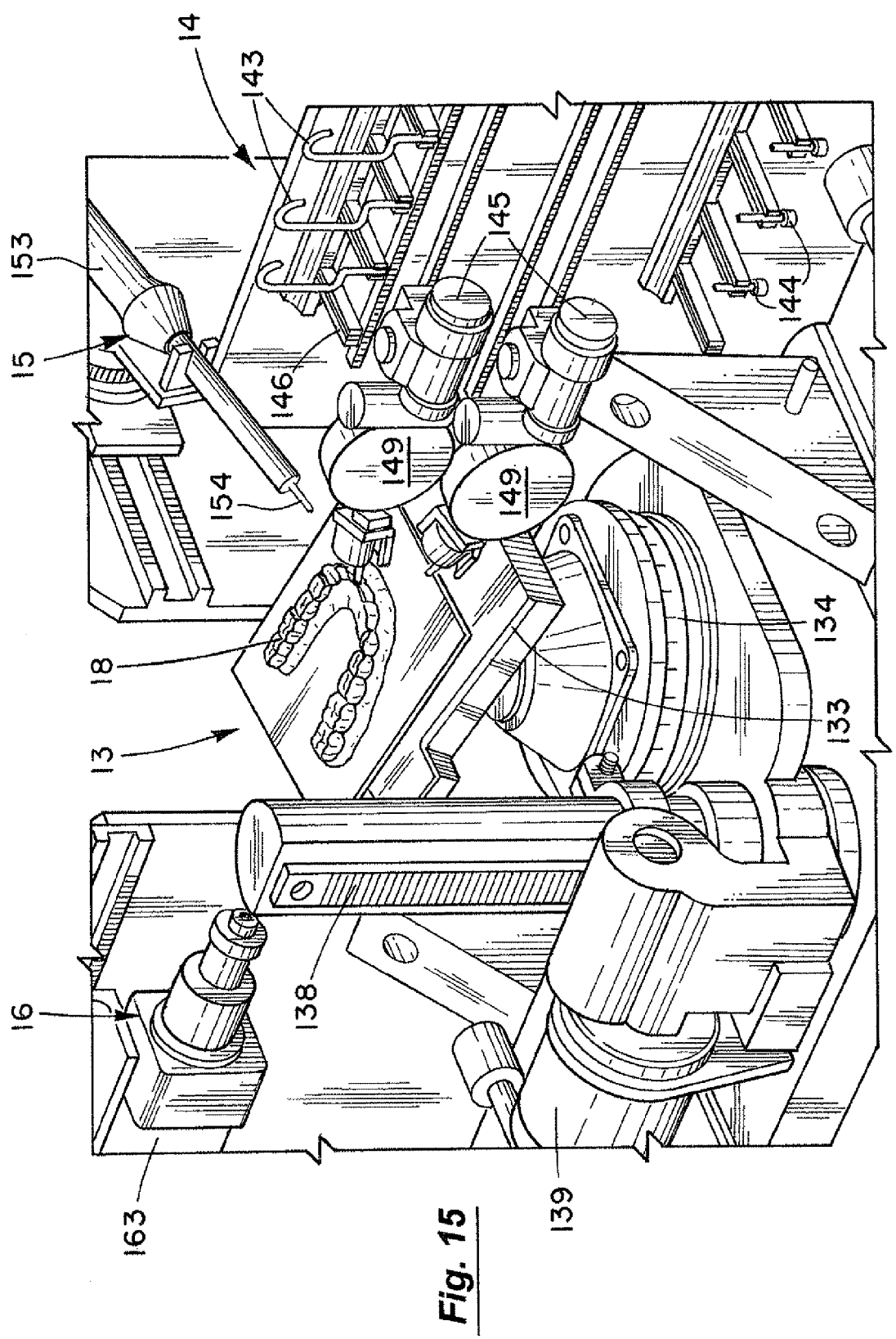
FIG. 15 is a detail perspective view of the thermoforming station 14 and THERMOAIRE localized heater station 15 being used to form a feature in an aligner 18 mounted on the turntable and lift platen 13.
Figure 16:
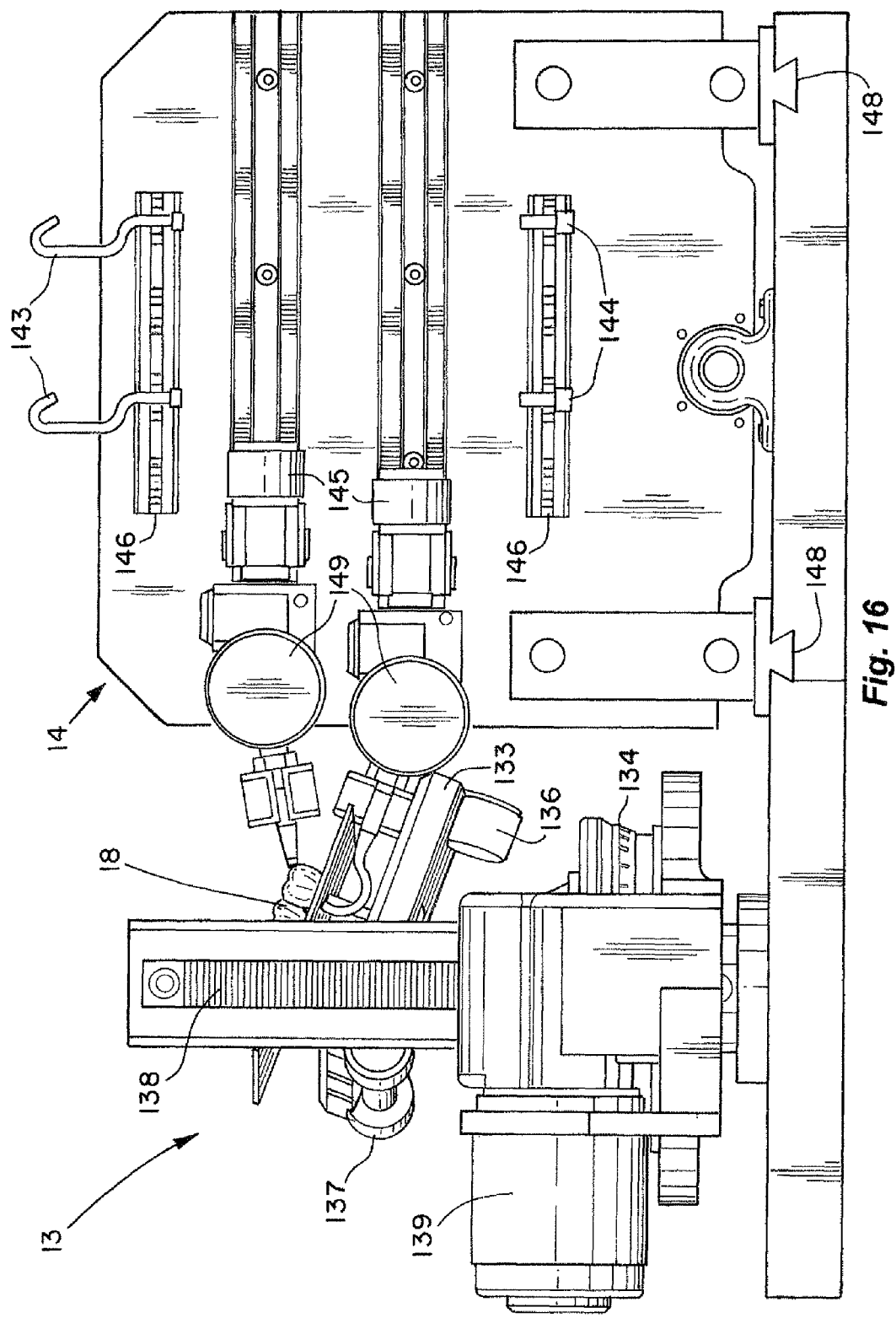
FIG. 16 is a side elevational view of the thermoforming station 14, aligner 18, and turntable and lift platen 13 corresponding to FIG. 15.

In the description above, the THERMOAIRE localized heater pencil 153 and its tip 154 serve to heat a small predetermined target region of the aligner 18. Once heated to a predetermined softening temperature, the aligner 18 quickly rotates 90.degree. to be oriented toward the thermoforming station 14 of the machine from whence the thermoforming dies are wielded. FIGS. 15 and 16 illustrate operation of the thermoforming station 14 to create a feature in an aligner 18. FIG. 15 depicts the central platen 13 after it has lifted the aligner 18 to a predetermined vertical level and rotated the aligner 18 clockwise (as viewed from above) toward the thermoforming station 14. The maxillary central right compartment of the aligner 18 has been oriented so as to be perpendicular to the axis of the thermoforming station 14. The declination table 133 has tilted the aligner 18 downward so that a pre-determined target point is tangent to the thermoforming axis. In addition, the upper and lower thermoforming servos 145 have traveled to the left into their correct positions along the x-axis and the thermoforming dies 143, 144 are seen after swinging into position to install a bump along the incisal/labial edge of the central tooth on the aligner 18. The THERMOAIRE localized heater pencil 153 and the laser 163 are seen retracted into their home positions while idle.

It should be expressly understood that other types of heating could used in place of the THERMOAIRE localized heater pencil to selectively heat small regions of the aligner. For example, a laser or a small radiant heater could be used for this purpose. The target region of the aligner could also be heated by contact with an electrically-heated element.

The reader is asked to appreciate that the transition motion involved in rotating the aligner by 90° clockwise as viewed from above for example involves a transposition of coordinate systems within the CAD portion 11 of the robotic system 9. Before the rotation, the X, Y and Z coordinates of the platen 13 were meshed with the X, Y and Z coordinates of the THERMOAIRE localized heater heating station 15, allowing stepper and servo activation of those two stations to be orchestrated by the CAM portion 12 of the machine as if the turntable and lifting platen 13 and the THERMOAIRE localized heater heating station 15 were one contiguous extension of the same coordinate system. To maintain the virtual registration of the aligner after the turntable rotated it 90°, the coordinate system of the THERMOAIRE heating station 15 was supplanted by the coordinate system of the thermoforming station 14. Stated differently, the positional values held by the THERMOAIRE heating station for "X" became "Y" values for the thermoforming station 14. Similarly, positional values for the THERMOAIRE Y axis were transposed into X values within the thermoforming station 14. Since the Z-axis was not affected by the rotation, the Z values were transitioned unchanged. In this manner then the aligner 18 may be processed through operations involving laser energy, thermoforming and THERMOAIRE-type alterations all within one pseudo-coordinate system. In practice, it is the coordinate system draped over the turntable and lifting platen 13 that is transposed to match any station actively altering the aligner 18 at any stage of the process. In this manner, the CAD/CAM portion of the robotic system 9 is always aware of the location and orientation of the aligner 18 relative to any station of the system in operation. This method of coordinate system transpositioning allows the coordinate system of the central platen 13 to operate seamlessly with multiple other stations oriented radially around it.

Figure 7:
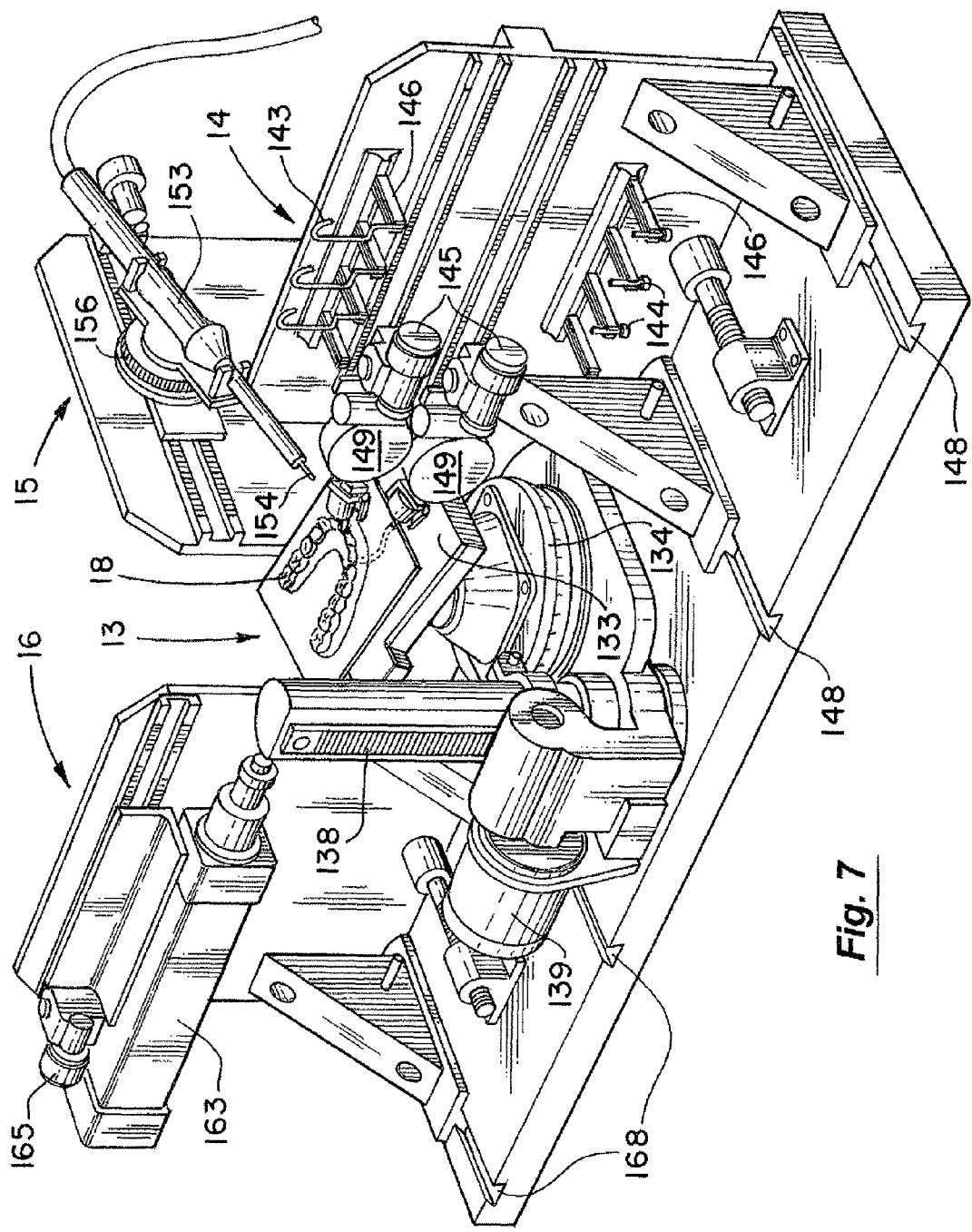
FIG. 7 is perspective view of an embodiment of the robotic system 9.
Figure 8:
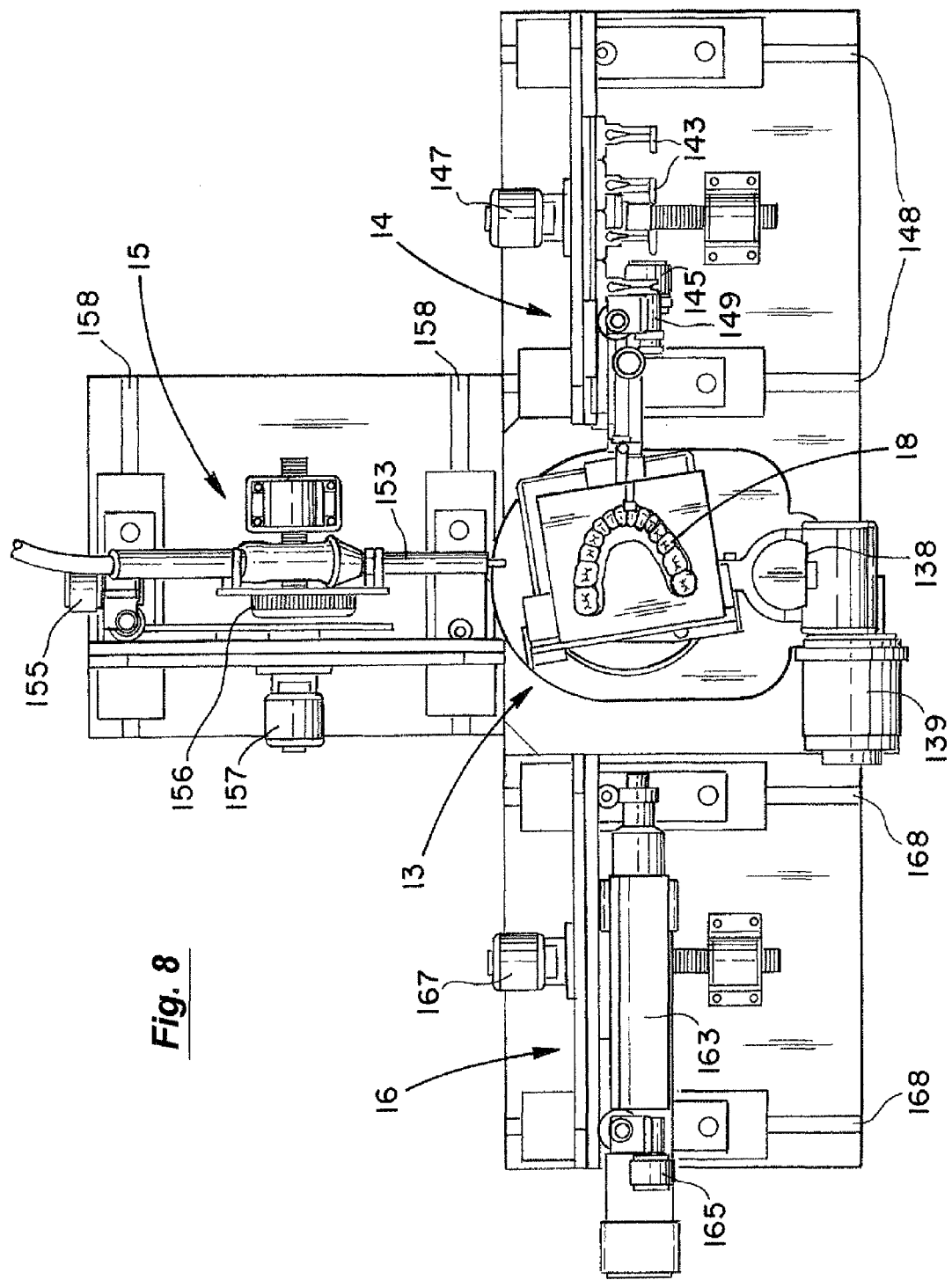
FIG. 8 is a top view of the robotic system 9 corresponding to FIG. 7.
Figure 9:
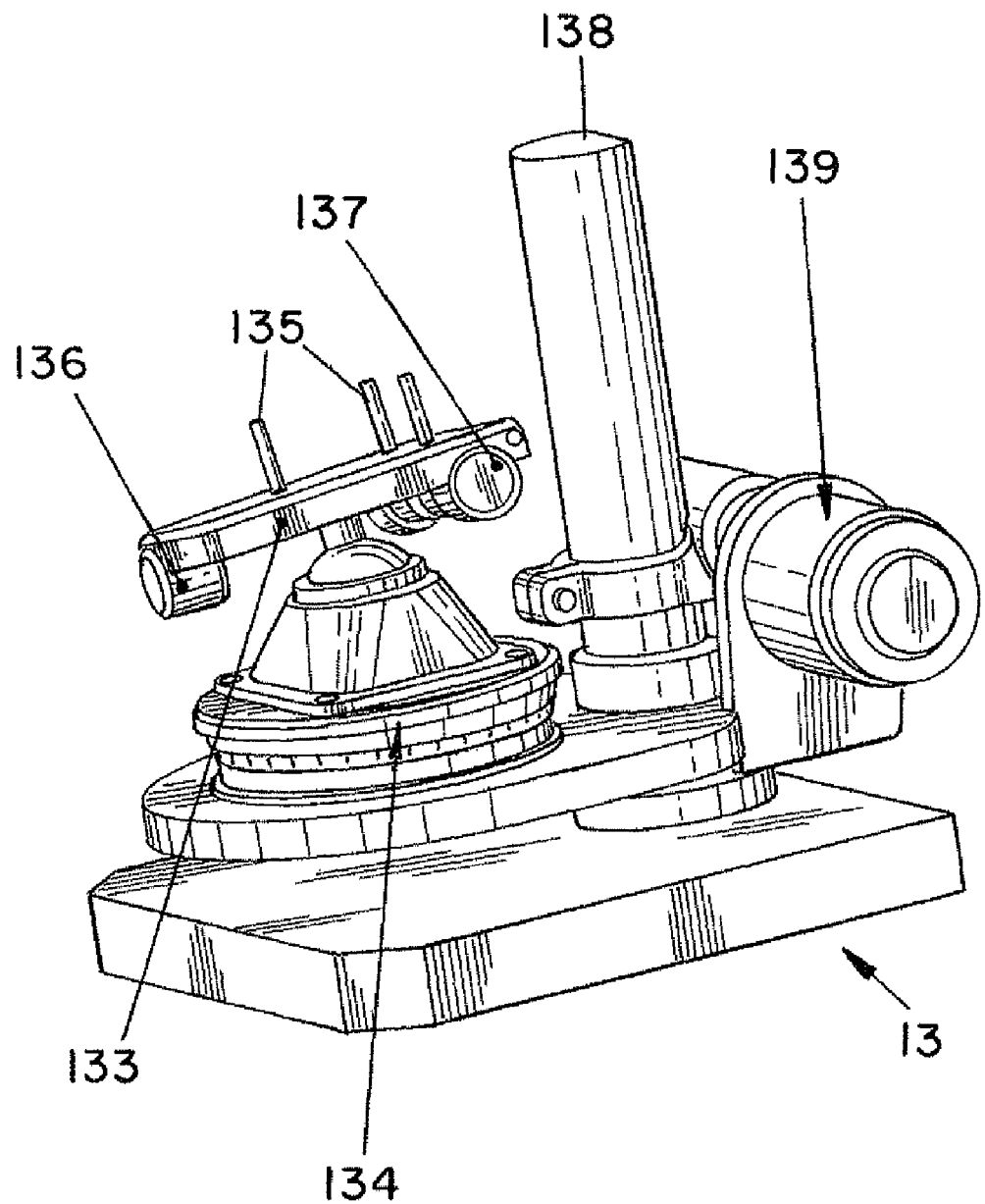
FIG. 9 is a detail perspective view of the turntable and lift platen 13 of the robotic system 9.

In the above description of the present invention, three robotic stations 14, 15 and 16 are laid out around the central platen 13 at its nine, twelve, and three o'clock positions, as shown in the perspective view provided in FIG. 7 and the top view provided in FIG. 8. In this same manner, a fourth station can be oriented at the six o'clock position. The various robotic stations 14, 15 and 16 described have been oriented at 90° orientations, but using a 60° orientation, six robotic stations can be oriented around a central platen 13. The present invention further anticipates that in this manner other robotic stations could be integrated above and/or below a central platen 13.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A robotic system for forming features in an orthodontic aligner having a thin polymeric shell, said robotic system comprising:
    a control system including a virtual model of the aligner;
    a platen controlled by the control system for three-dimensional positioning of the aligner;
    a heating station controlled by the control system selectively heating a small region of the aligner on the platen with a localized flow of heated air; and
    a thermoforming station controlled by the control system for manipulating the heated region of the aligner on the platen to form a desired feature in the aligner.

2. The robotic system of claim 1 wherein the control system further comprises CAD software for designing features in the aligner.

3. The robotic system of claim 1 wherein the heating station comprises a small hot air source.

4. The robotic system of claim 1 further comprising a laser cutting and trimming station controlled by the control system.

5. The robotic system of claim 1 wherein the thermoforming station further comprises multiple interchangeable tools for selectively forming any of a variety of features in the aligner.

6. A robotic system for forming features in an orthodontic aligner having a thin polymeric shell, said robotic system comprising:
    a control system including a virtual model of the aligner and CAD software enabling a user to design a feature in the aligner;
    a platen controlled by the control system for three-dimensional positioning of the aligner;
    a heating station controlled by the control system selectively heating a small region of the aligner on the platen with a localized flow of heated air for a feature; and
    a thermoforming station controlled by the control system for manipulating the heated region of the aligner on the platen to form the feature in the aligner.

7. The robotic system of claim 6 wherein the heating station comprises a small hot air source.

8. The robotic system of claim 6 further comprising a laser cutting and trimming station controlled by the control system.

9. The robotic system of claim 6 wherein the thermoforming station further comprises multiple interchangeable tools for selectively forming any of a variety of features in the aligner.

10. A robotic system for forming features in an orthodontic aligner having a thin polymeric shell, said robotic system comprising:
    a control system including a virtual model of the aligner;
    a platen controlled by the control system for three-dimensional positioning of the aligner; and
    a plurality of robotic stations arranged about the platen for performing actions to form a feature on the aligner on the platen under the control of the control system, said robotic stations including:
    (a) a heating station controlled by the control system selectively heating a small region of the aligner on the platen with a localized flow of heated air; and
    (b) a thermoforming station controlled by the control system for manipulating the heated region of the aligner on the platen to form a desired feature in the aligner.

11. The robotic system of claim 10 wherein the control system further comprises CAD software for designing features in the aligner.

12. The robotic system of claim 10 wherein the heating station comprises a small hot air source.

13. The robotic system of claim 10 further comprising a laser cutting and trimming station controlled by the control system.

14. The robotic system of claim 10 wherein the thermoforming station further comprises multiple interchangeable tools for selectively forming any of a variety of features in the aligner.

* * * * *